(12) United States Patent
Giger et al.

(10) Patent No.: US 8,894,663 B2
(45) Date of Patent: Nov. 25, 2014

(54) REMOTELY ADJUSTABLE TISSUE DISPLACEMENT DEVICE

(75) Inventors: Lukas Giger, Basel (CH); Bruno Laeng, Horriwil (CH); Hugo Flueckiger, Derendingen (CH); Markus Hunziker, Aarau (CH)

(73) Assignee: DePuy Synthes Products, LLC, Raynham, MA (US)

( * ) Notice: Subject to any disclaimer, the term of this patent is extended or adjusted under 35 U.S.C. 154(b) by 589 days.

(21) Appl. No.: 13/230,042

(22) Filed: Sep. 12, 2011

(65) Prior Publication Data

US 2012/0004692 A1     Jan. 5, 2012

Related U.S. Application Data

(62) Division of application No. 11/697,085, filed on Apr. 5, 2007, now Pat. No. 8,016,837.

(60) Provisional application No. 60/790,589, filed on Apr. 6, 2006, provisional application No. 60/866,739, filed on Nov. 21, 2006.

(51) Int. Cl.
| | |
|---|---|
| *A61B 17/58* | (2006.01) |
| *A61B 17/60* | (2006.01) |
| *A61F 2/00* | (2006.01) |
| *A61B 17/80* | (2006.01) |
| *A61B 17/00* | (2006.01) |

(52) U.S. Cl.
CPC ... *A61B 17/8076* (2013.01); *A61B 2017/00407* (2013.01); *A61B 2017/00411* (2013.01); *A61B 2017/00867* (2013.01); *A61B 17/8009* (2013.01)
USPC ...................................................... 606/105

(58) Field of Classification Search
USPC .............. 606/105, 57, 282, 90, 71, 257–258, 606/280, 902–906
See application file for complete search history.

(56) References Cited

U.S. PATENT DOCUMENTS

| | | | |
|---|---|---|---|
| 3,976,060 | A | 8/1976 | Hildebrandt et al. |
| 4,615,338 | A | 10/1986 | Ilizarov et al. |
| 5,092,889 | A | 3/1992 | Campbell, Jr. |

(Continued)

FOREIGN PATENT DOCUMENTS

| | | |
|---|---|---|
| CN | 1043439 | 7/1990 |
| CN | 1046277 | 10/1990 |

(Continued)

OTHER PUBLICATIONS

Office Action and Supplementary Search Report, dated Nov. 28, 2012, received from the China Patent Office in connection with Chinese Patent Application No. 200780021107.2 (English translation).

(Continued)

*Primary Examiner* — Sameh Boles
(74) *Attorney, Agent, or Firm* — Meunier Carlin & Curfman, LLC

(57) ABSTRACT

The invention relates to an apparatus for displacing tissue within the body, wherein the apparatus includes two or more attachment members selectively displaceable with respect to each other via a driving member. The driving member preferably is rotatable and is caused to rotate by a magnetic actuator that can be activated by a magnetic field from outside the body.

8 Claims, 17 Drawing Sheets

(56) References Cited

U.S. PATENT DOCUMENTS

| | | | |
|---|---|---|---|
| 5,413,602 A | 5/1995 | Metz-Stavenhagen | |
| 5,626,579 A | 5/1997 | Muschler et al. | |
| 5,704,939 A | 1/1998 | Justin | |
| 5,720,746 A | 2/1998 | Soubeiran | |
| 6,336,929 B1 * | 1/2002 | Justin .............................. | 606/63 |
| 6,796,984 B2 | 9/2004 | Soubeiran | |
| 6,918,910 B2 | 7/2005 | Smith et al. | |
| 6,972,020 B1 | 12/2005 | Grayson et al. | |
| 7,011,658 B2 | 3/2006 | Young | |
| 2002/0156480 A1 | 10/2002 | Overes et al. | |
| 2002/0161374 A1 | 10/2002 | Cohen et al. | |
| 2005/0234448 A1 | 10/2005 | McCarthy | |
| 2005/0245928 A1 | 11/2005 | Colleran et al. | |
| 2005/0246034 A1 | 11/2005 | Soubeiran | |
| 2006/0036259 A1 | 2/2006 | Carl et al. | |
| 2006/0228982 A1 | 10/2006 | Rehkemper et al. | |
| 2007/0270803 A1 | 11/2007 | Giger et al. | |
| 2008/0003042 A1 | 1/2008 | Wu et al. | |

FOREIGN PATENT DOCUMENTS

| | | |
|---|---|---|
| CN | 2119205 | 10/1992 |
| CN | 1286074 | 3/2001 |
| FR | 2834200 | 7/2003 |
| JP | 9056736 | 3/1997 |
| SU | 865284 | 9/1981 |
| WO | 9951160 | 10/1999 |
| WO | 02056777 A1 | 7/2002 |
| WO | 02071962 A1 | 9/2002 |
| WO | 2004/019796 | 3/2004 |
| WO | 2004058083 A1 | 7/2004 |
| WO | 2007118179 A3 | 10/2007 |
| WO | 2007144489 A2 | 12/2007 |
| WO | 2008/040880 | 4/2008 |

OTHER PUBLICATIONS

Vertical Expandable Prosthetic Titanium Rib (VEPTR) Technique Guide, Synthes Spine, 2007, 44 pages.

International Search Report, dated Feb. 5, 2008, received from the European Patent Office in connection with International Publication No. WO2007/118177.

U.S. Official Action, dated Dec. 22, 2011, received in connection with corresponding U.S. Appl. No. 11/697,110.

* cited by examiner

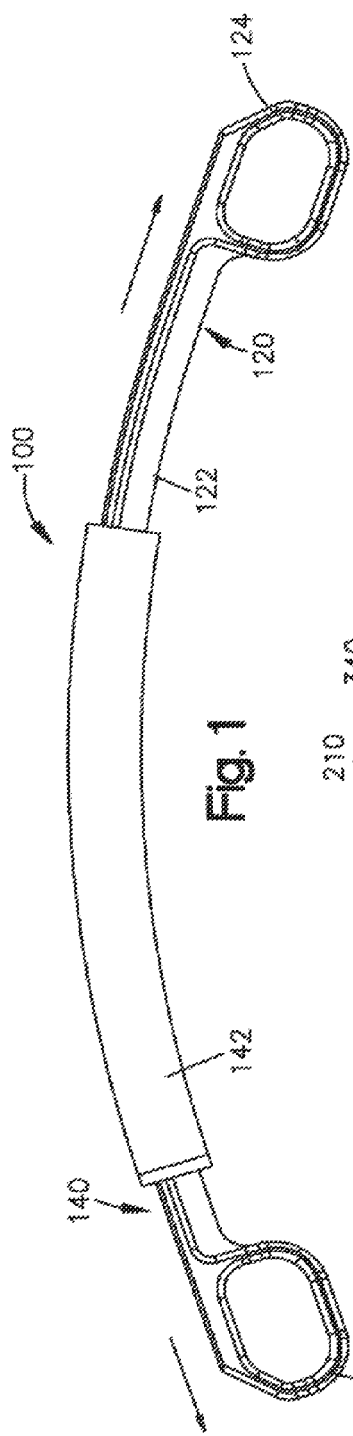
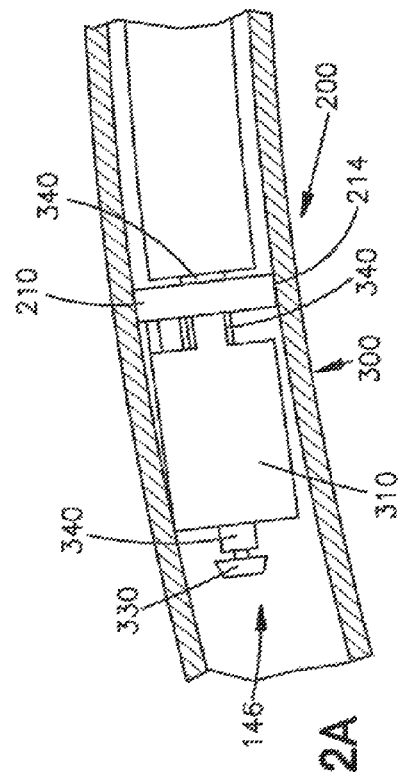
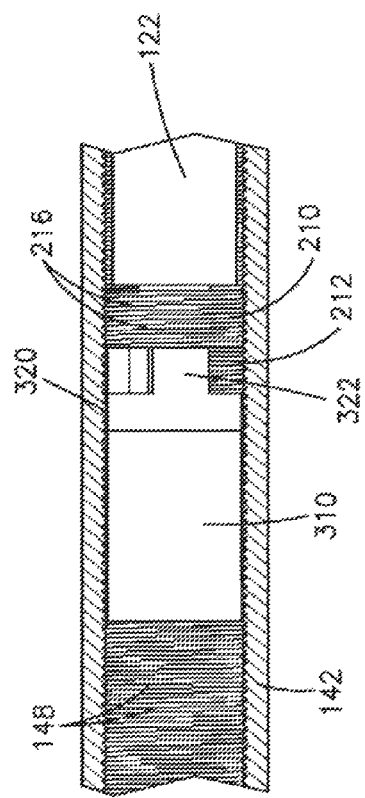
Fig. 1
Fig. 2A
Fig. 2B

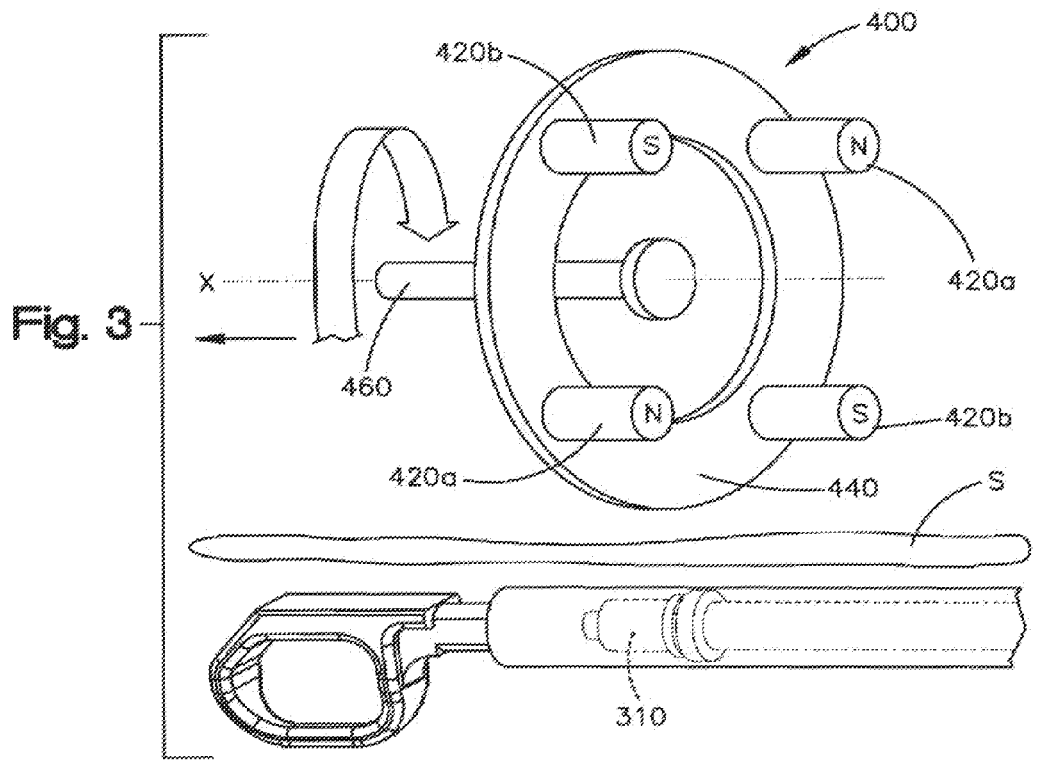
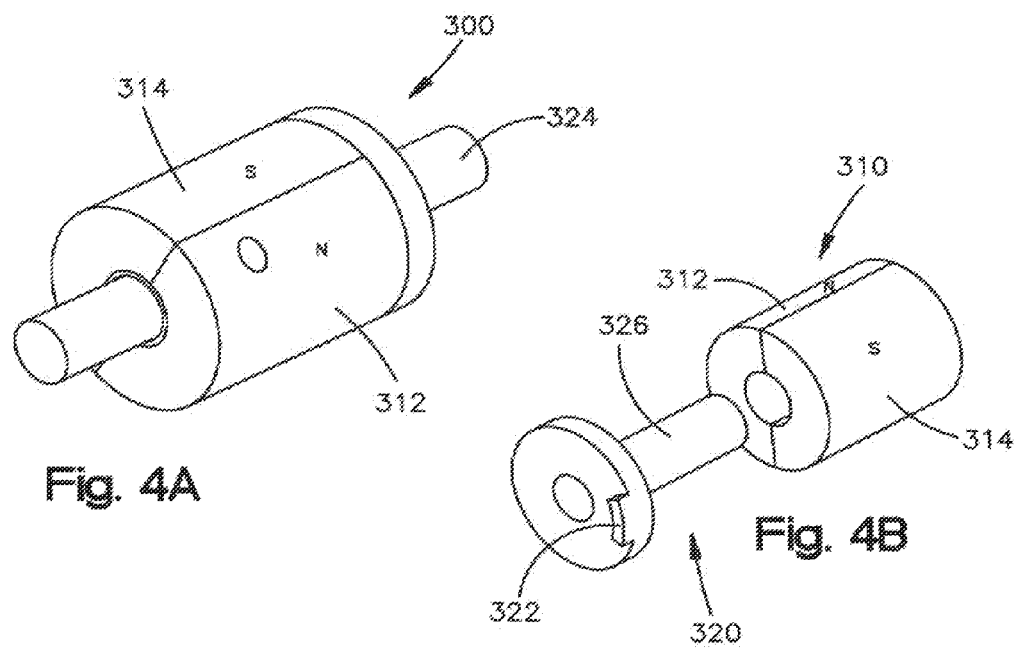

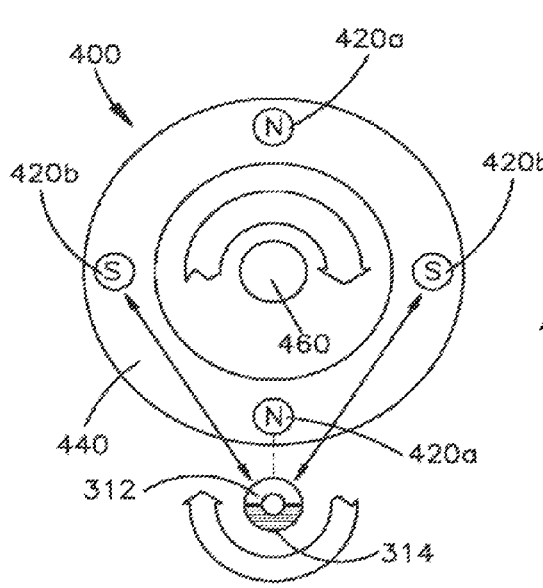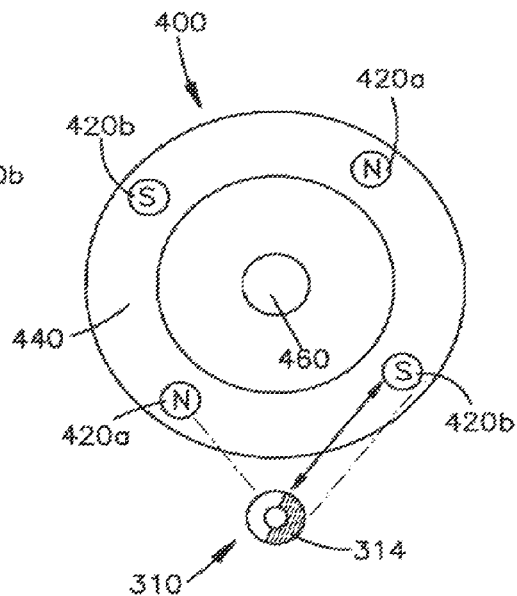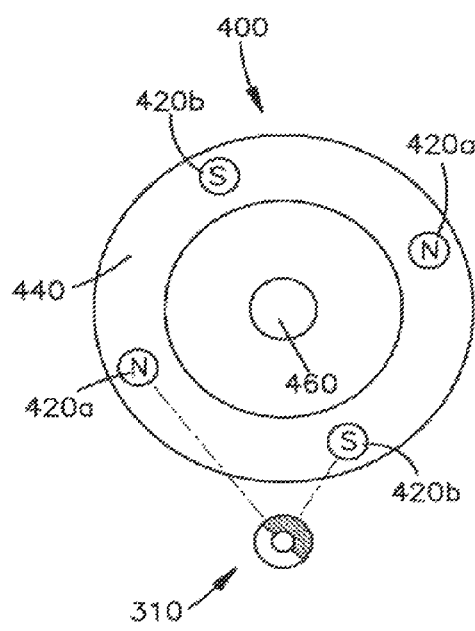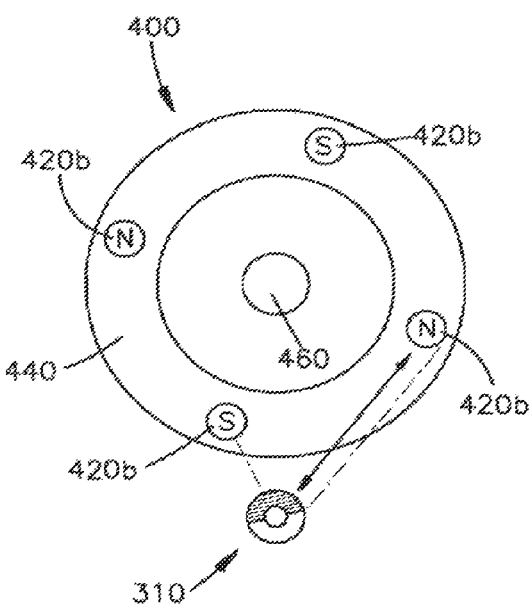

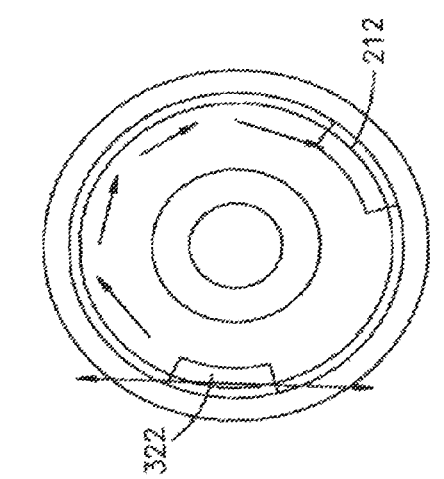
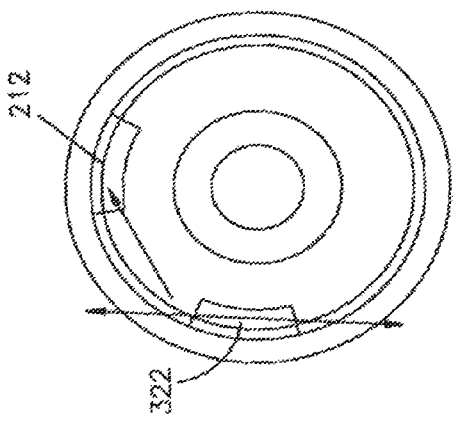
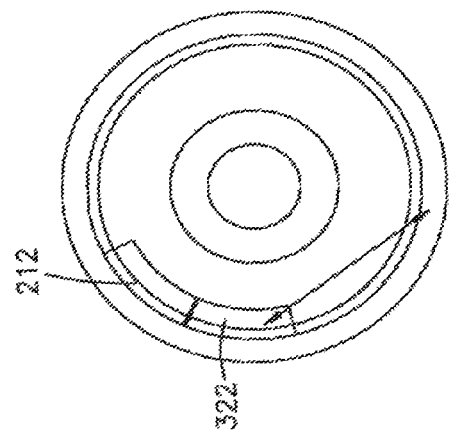
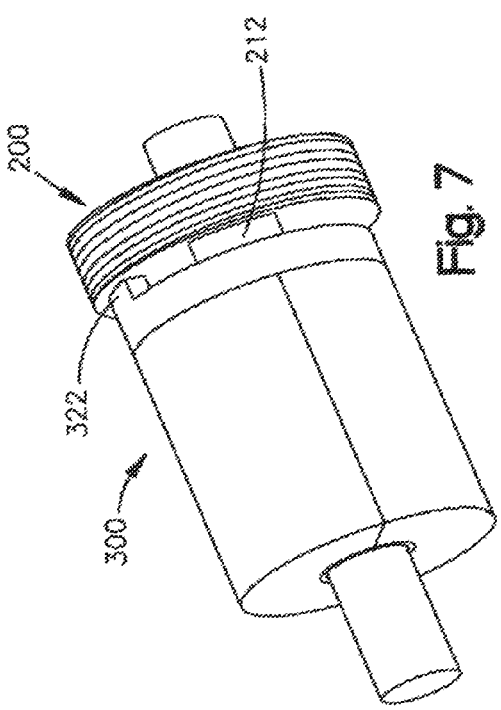

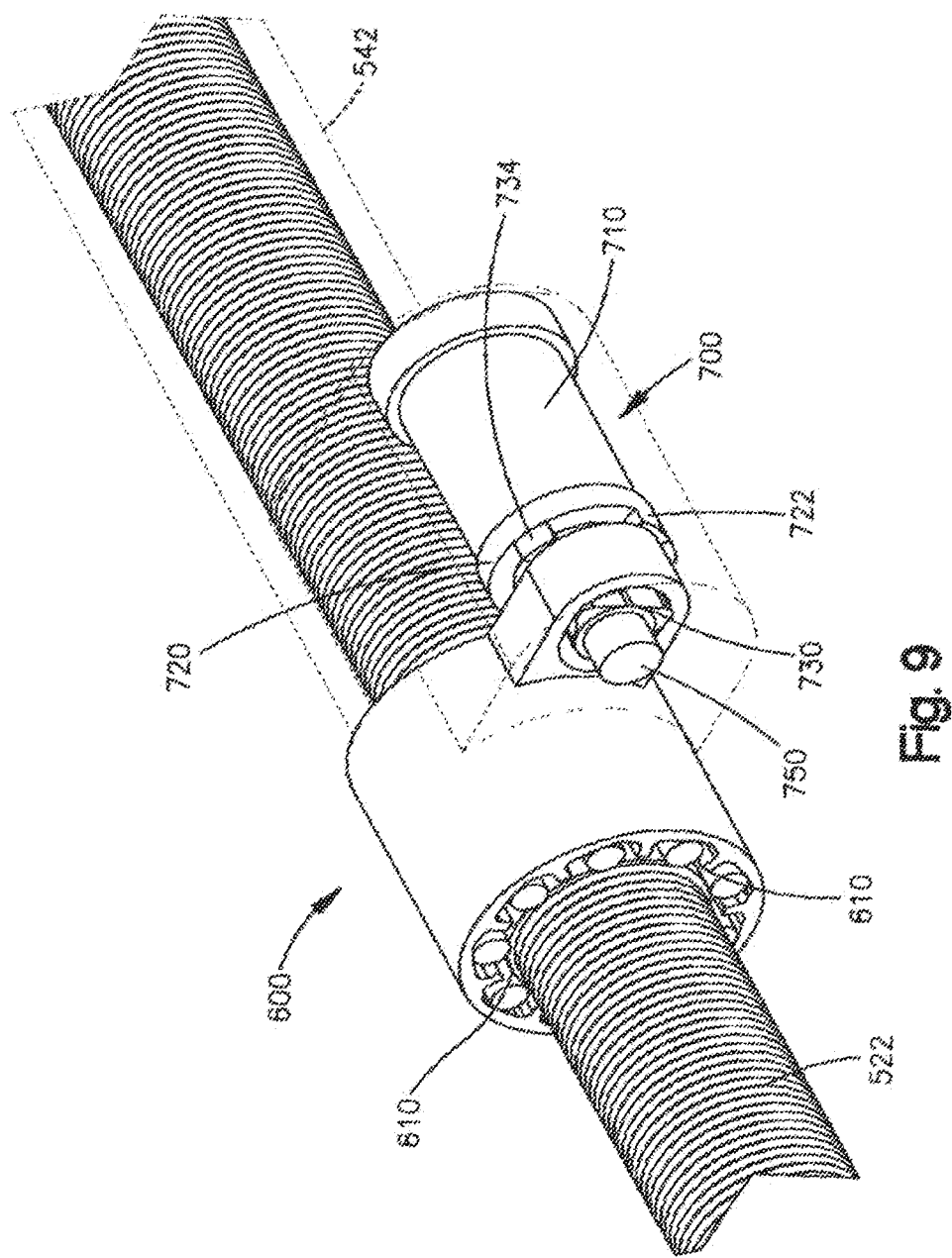

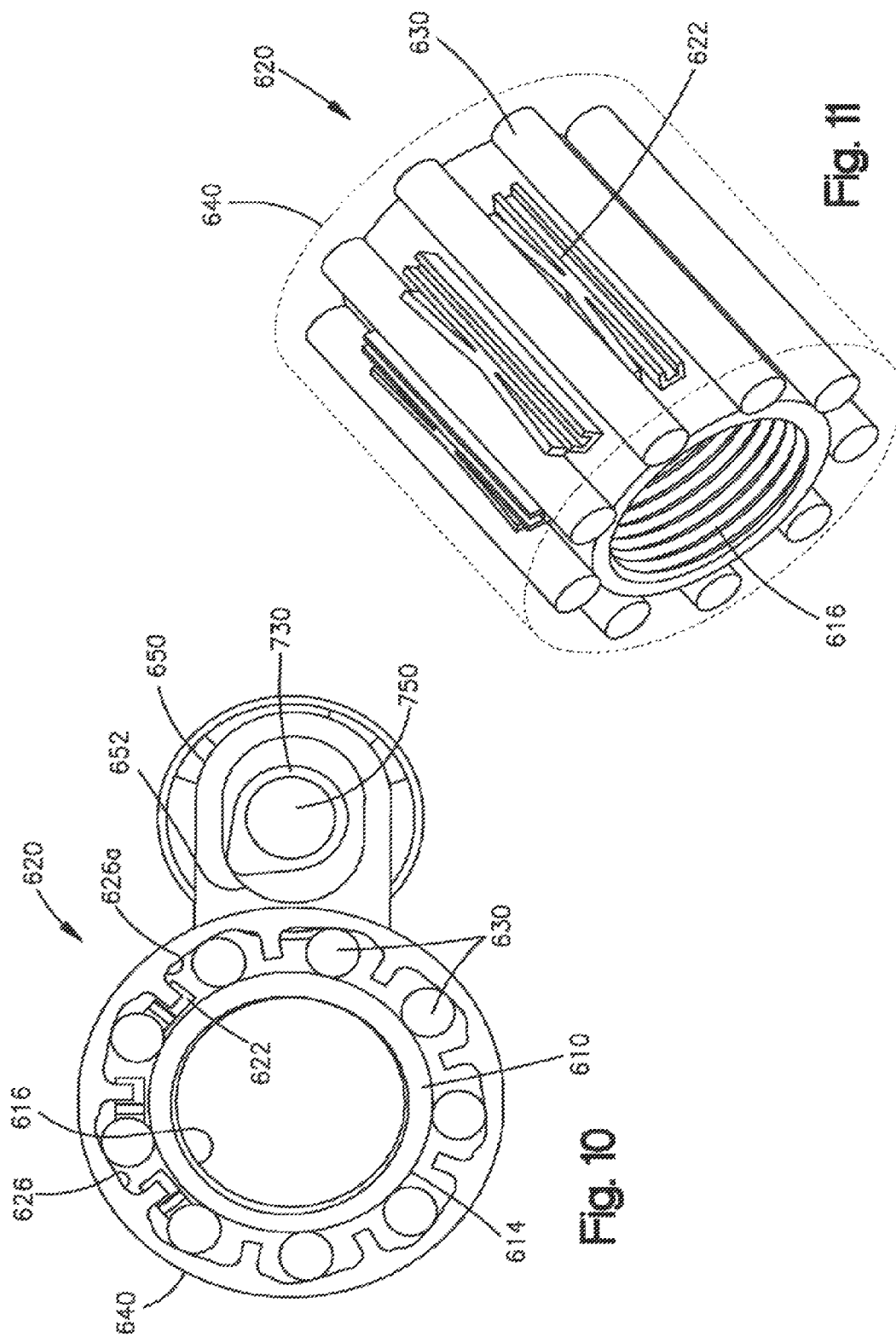

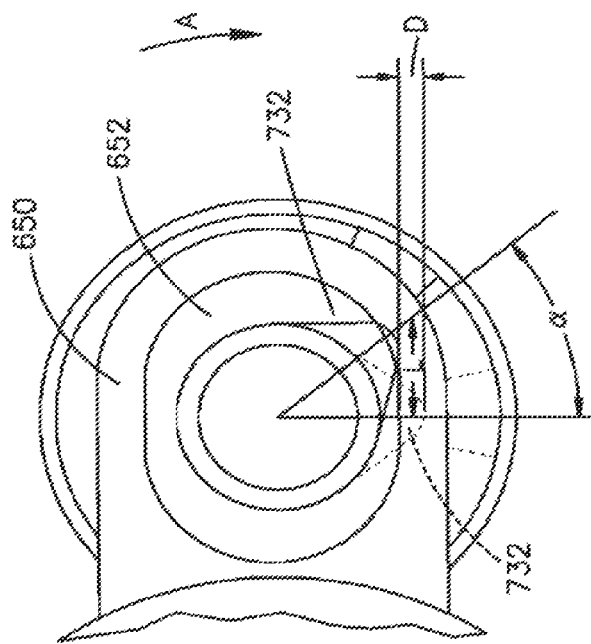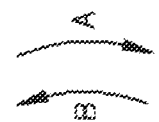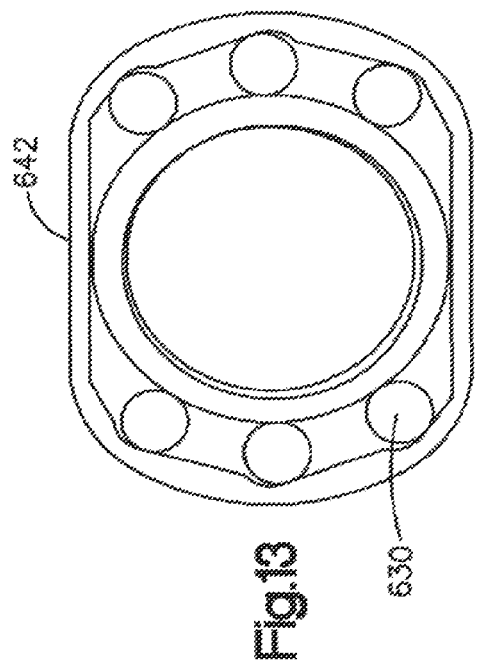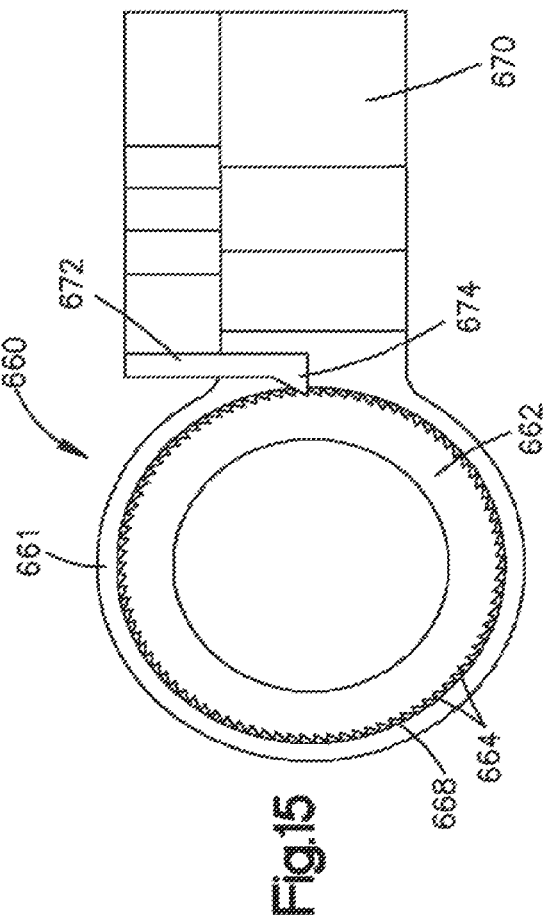

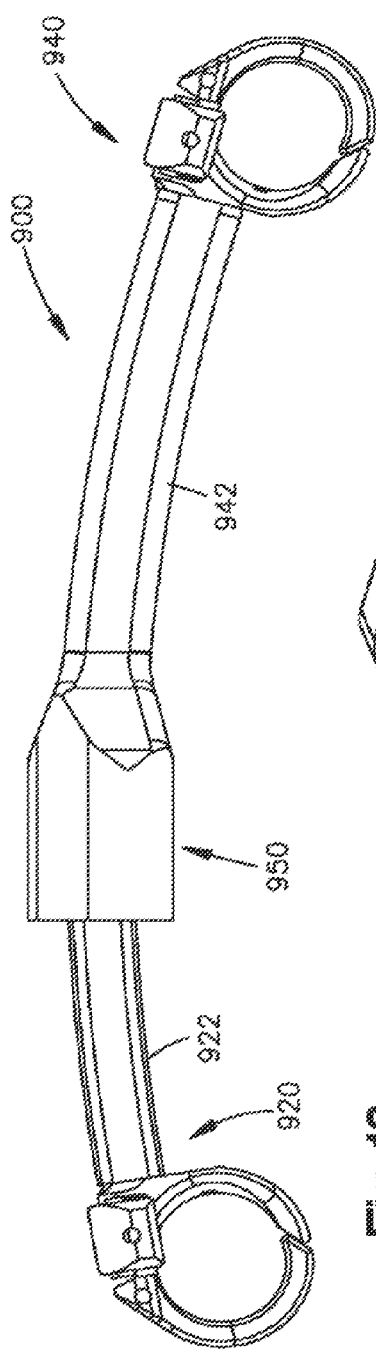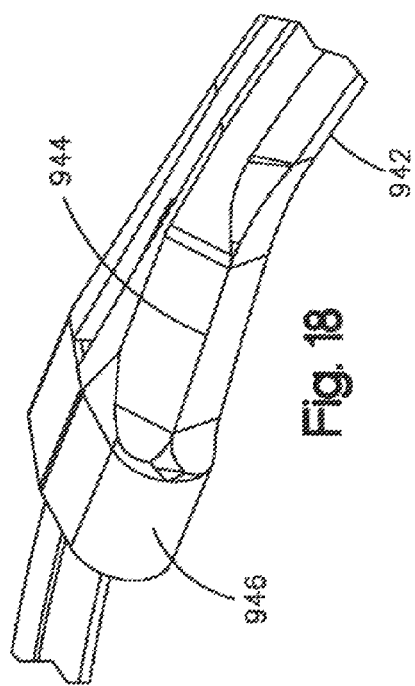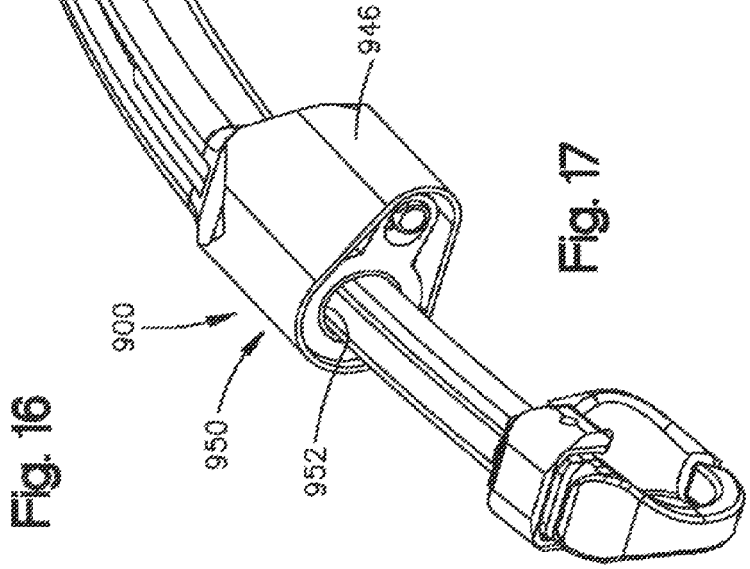

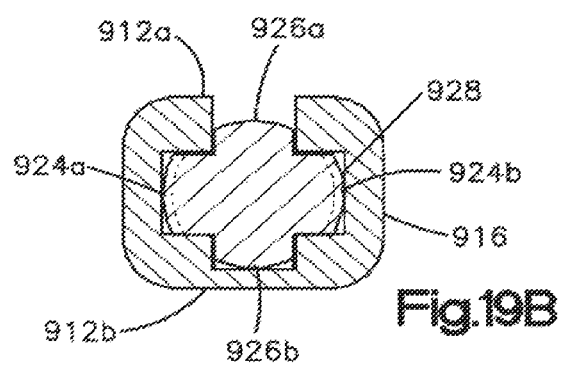
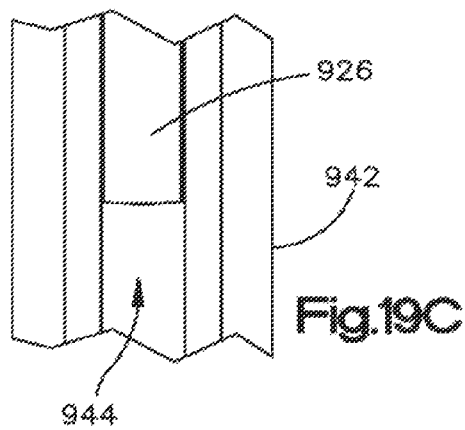
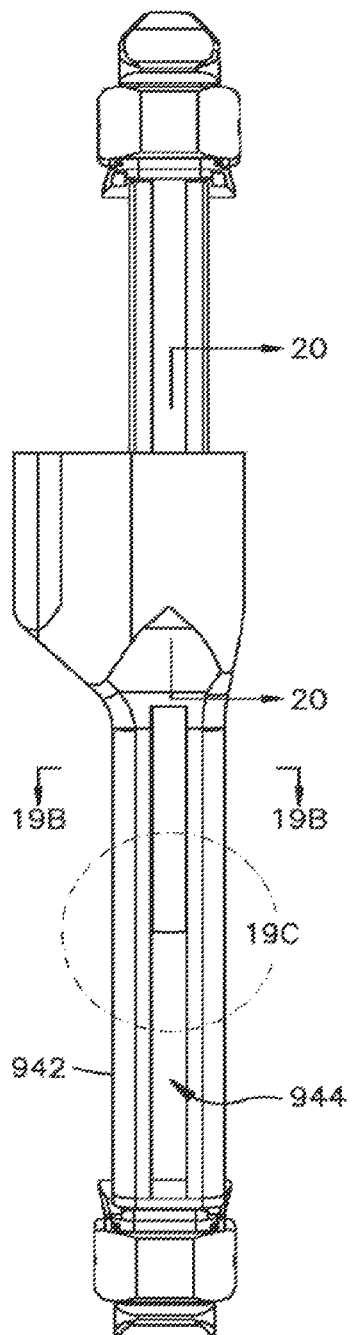
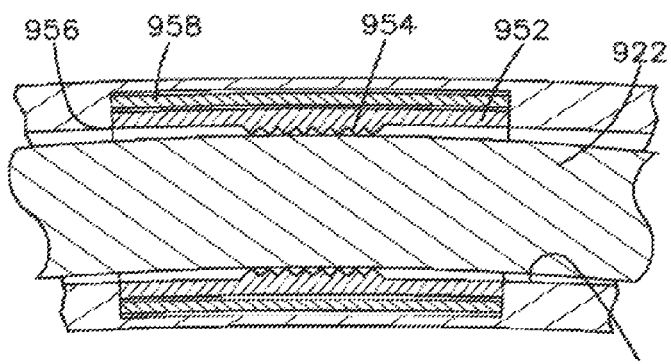

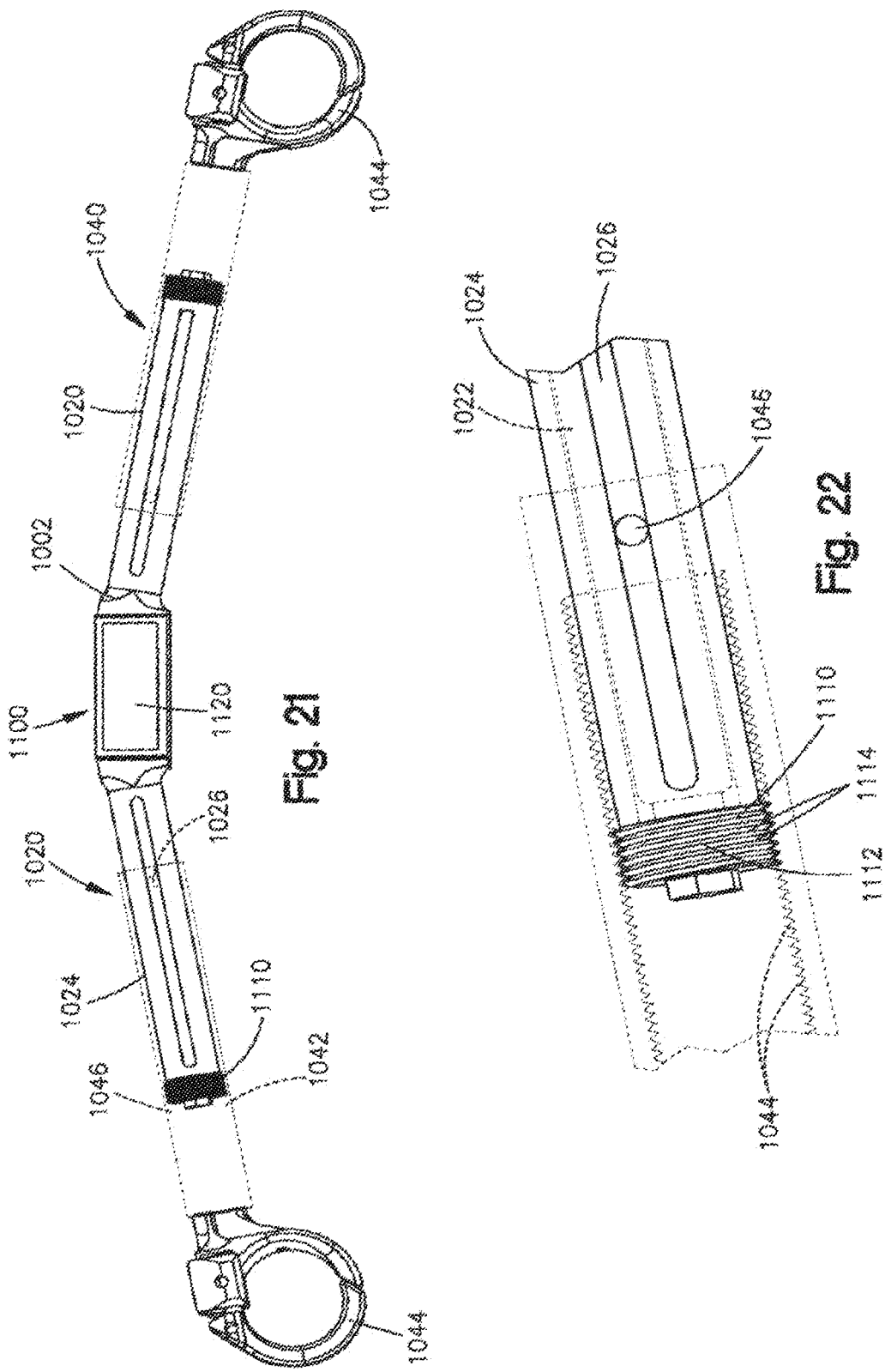

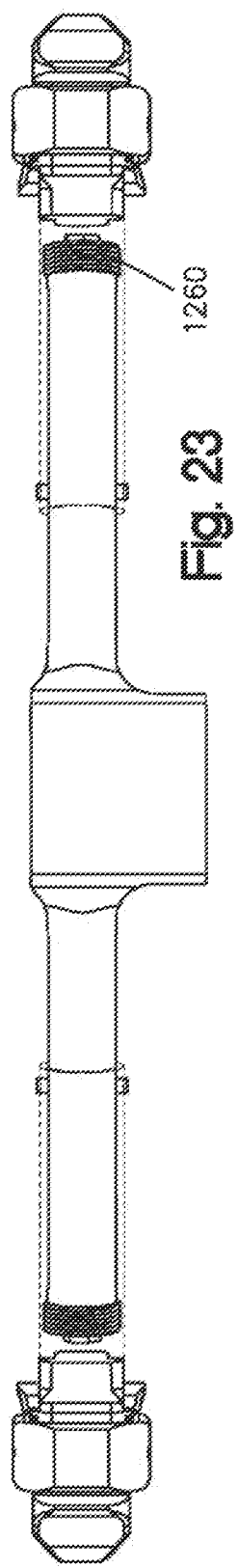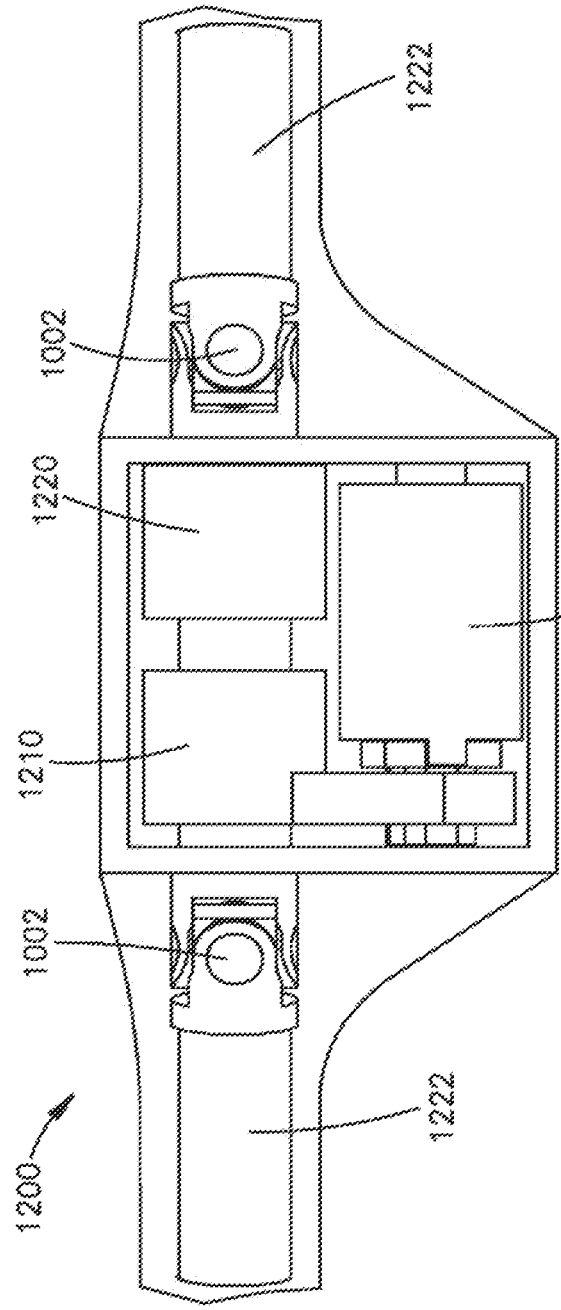

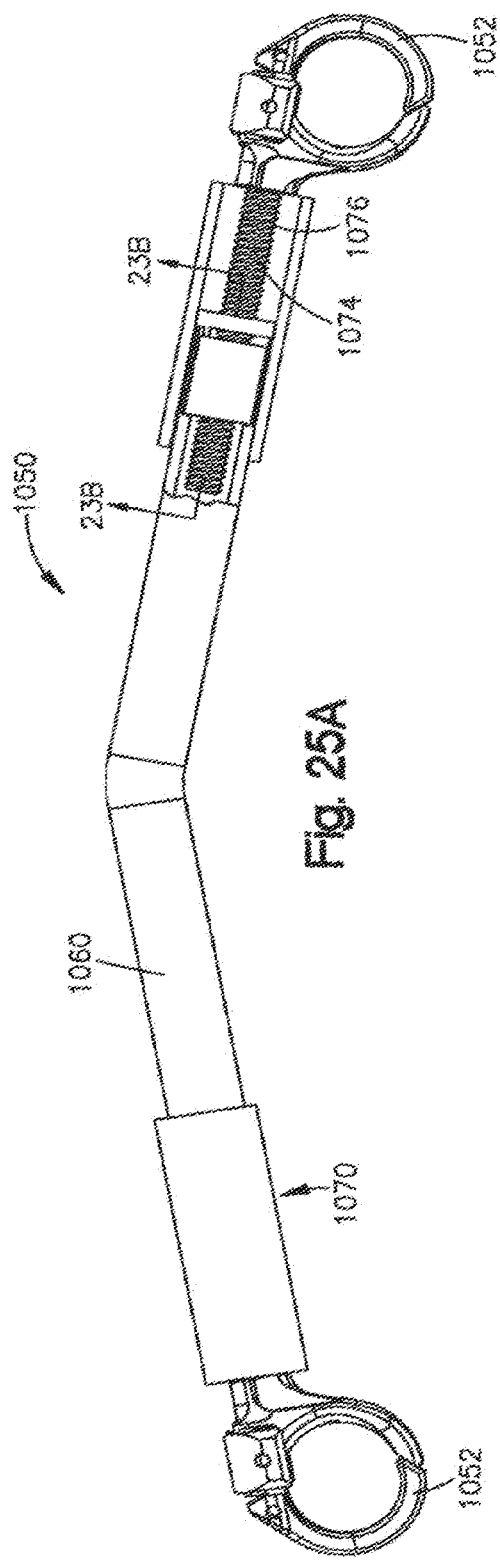
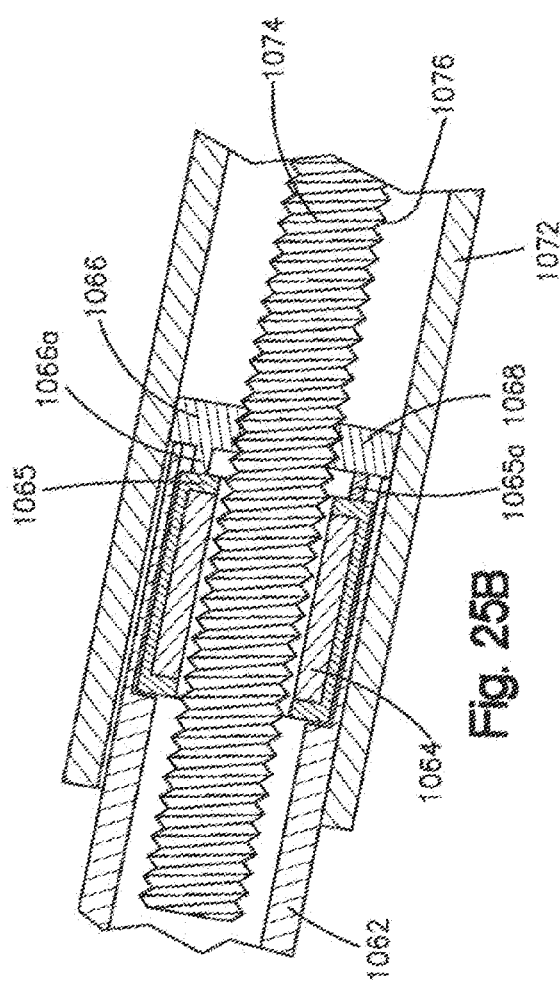
Fig. 25A
Fig. 25B

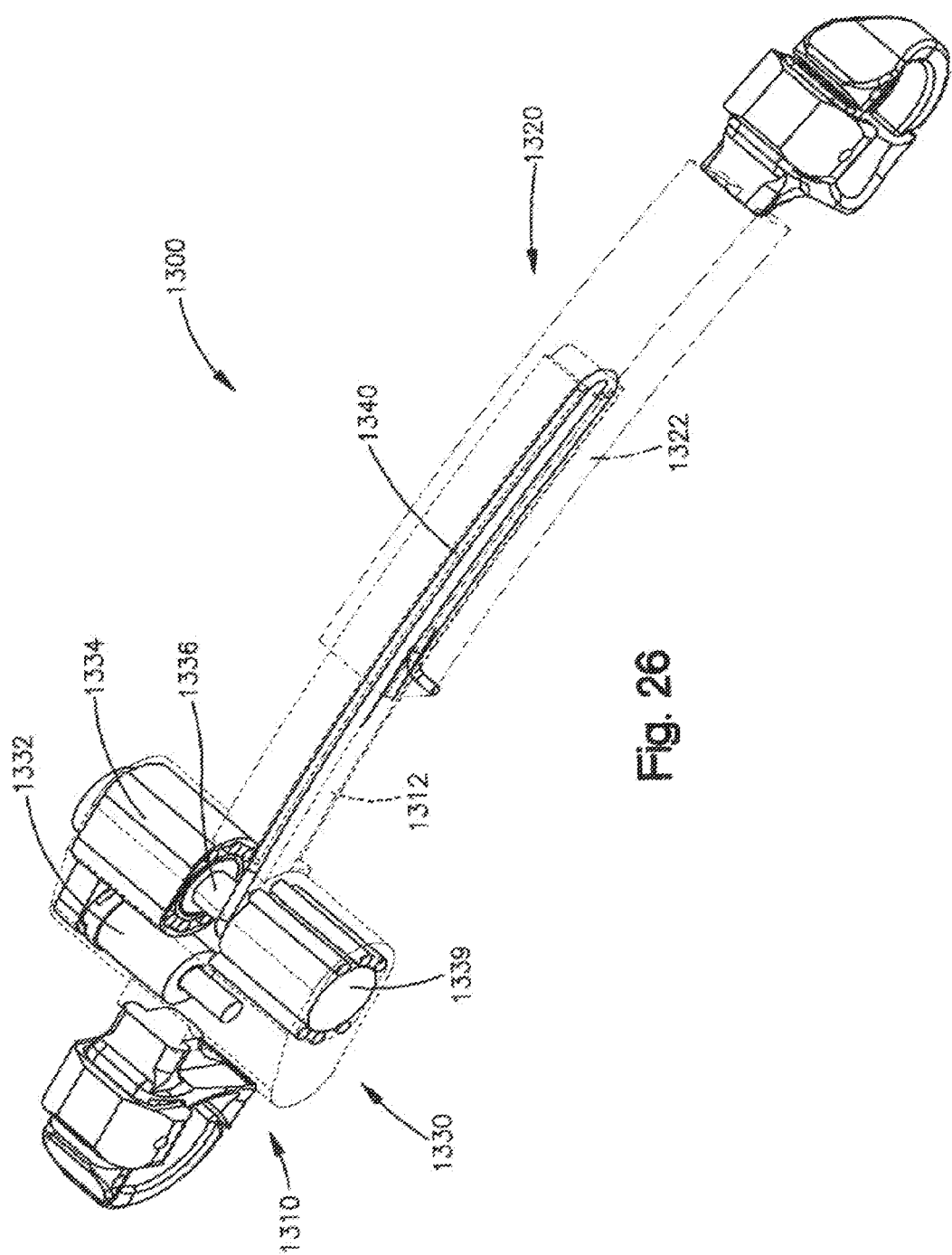

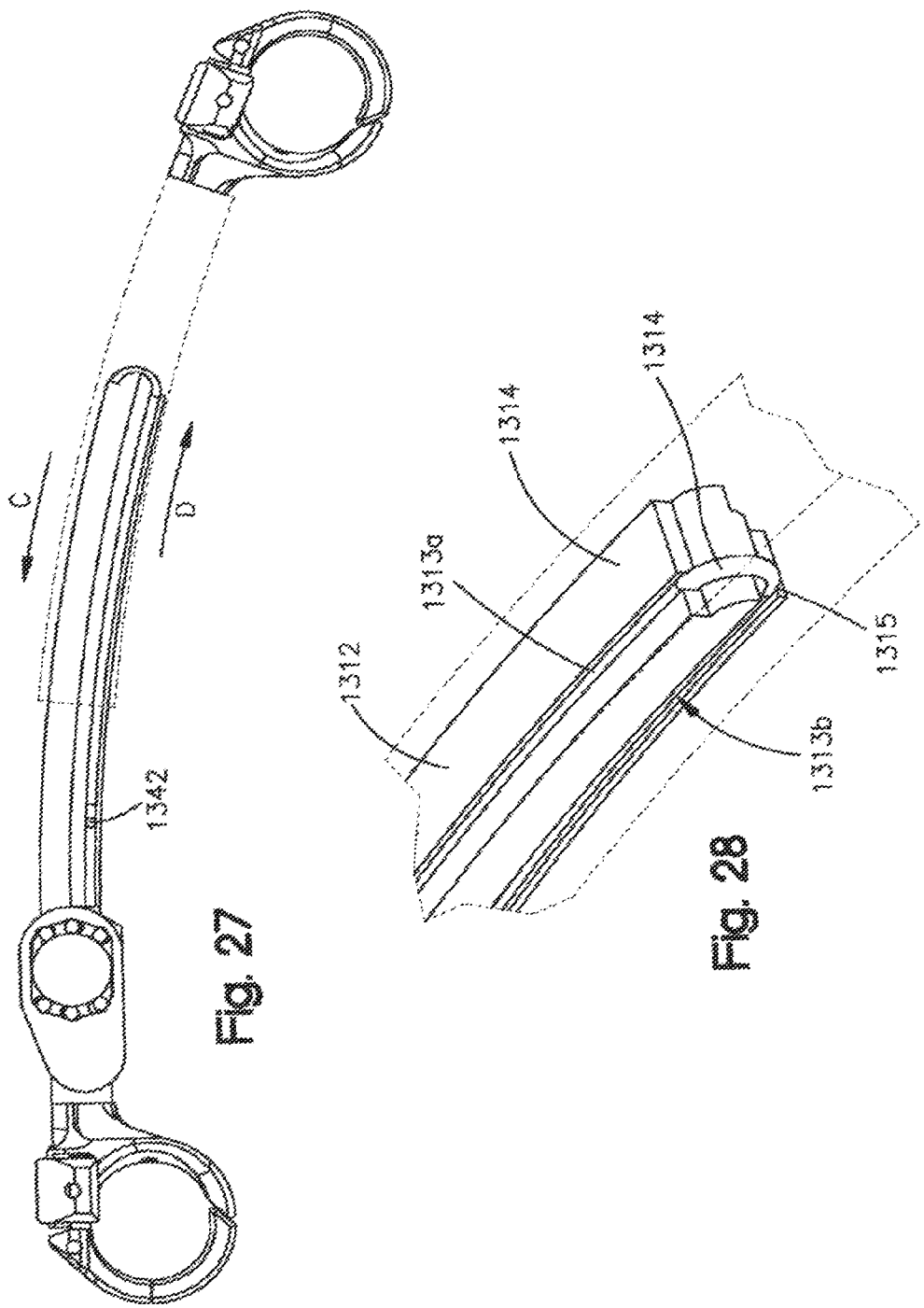

REMOTELY ADJUSTABLE TISSUE DISPLACEMENT DEVICE

CROSS-REFERENCE TO RELATED APPLICATIONS

This application is a division of U.S. patent application Ser. No. 11/697,085, filed Apr. 5, 2007, entitled "REMOTELY ADJUSTABLE TISSUE DISPLACEMENT DEVICE," which is incorporated herein by reference in its entirety. This application also claims the benefit of U.S. Provisional Application Ser. No. 60/790,589 filed on Apr. 6, 2006, entitled "REMOTELY ADJUSTABLE EXPANDABLE DEVICE" and U.S. Provisional Application Ser. No. 60/866,739 filed on Nov. 11, 2006, entitled "REMOTELY ADJUSTABLE BONE DISPLACEMENT DEVICE", both of which are hereby incorporated in their entirety by reference.

TECHNICAL FIELD OF THE INVENTION

The invention generally relates to a device for displacing tissue within a body, such as one or more bones of an animal. More specifically, the invention relates to implants within a patient that can be remotely adjusted from outside the body to extend and/or contract.

BACKGROUND OF THE INVENTION

Expandable implants such as the system commercially available by Synthes, Inc. under the trademark VEPTR® (Vertically Expandable Prosthetic Titanium Rib) system are used to displace bones within a patient. For example, small children with heavy spinothoracic deformities often use such implants attached to the ribs, spine and/or pelvis. The implant is adjusted, usually at regular intervals such as every 6 months, through small skin incisions. However, the adjustment often requires general anesthesia and hospital stay to recover from the adjustment procedure, and also introduces a risk of infection.

SUMMARY OF THE INVENTION

Generally speaking, a device for moving tissue, such as an implant for displacing bone is provided. The device can include two elongated members displaceable, preferably telescopically displaceable, with respect to each other to extend and contract relative to the length of the device. A drive member can rotate to extend and/or contract the device, and is preferably rotated by a magnetic actuator. The magnetic actuator is preferably rotatable by an external magnetic field. More specifically, a magnetic field outside the patient's body can be utilized to extend and/or contract the implant within the patient's body.

One embodiment of the device includes two elongated members having a proximal end and a distal end, a drive member operably associated with and rotatable relative to one of the elongated members. A magnetic actuator assembly may be provided which is associated with the drive member in such a way that when the magnetic actuator is rotated, the drive member is also rotated, which causes the two elongated members to move relative to each other. The magnetic actuator assembly is preferably rotatable by an external magnetic field.

Another embodiment of the device comprises two bone attachment members and a displacement mechanism configured for subcutaneous implantation in a position accessible by a magnetic field transmitted through the skin. The device includes a driven member and a rotatable driving member coupled between the bone attachment members, a lip coupled to the driving member, a magnet rotatable back and forth in opposite directions, and a drive tooth coupled to the magnet to contact, tap or impact against the lip upon back and forth rotation of the magnet.

An alternate embodiment of the device comprises a bone displacement apparatus having two bone attachment members, a driven member coupled to one of the bone attachment members, and a rotatable driving member coupled to the second bone attachment member. Preferably, the driving member and the driven member are associated via screw threads to move the driven member axially relative to the second bone attachment member. Therefore, upon rotation of the driving member in a displacement direction, the bone attachment members can be displaced. The device may also include a rotatable actuator and a clutch mechanism operative between the actuator and the driving member, such that upon rotation of the actuator back and forth in opposite directions, the driving member is advanced in the displacement direction. Preferably, a rotatable magnet is provided, wherein the rotation of the magnet results in the actuator rotating back and forth.

In accordance with a preferred embodiment of the device, a changing magnetic field of a magnetic rotor may be used to rotate the drive member, rather than direct actual magnetic force. For example, the drive member or actuator for rotating the drive member may oscillate and rely upon impact momentum for such a rotation.

The device may comprise the features of construction, combination of elements, and arrangement of parts which will be exemplified in the construction hereinafter set forth, but the scope of the invention should not be limited to such features, combination of elements or arrangement of parts.

The invention accordingly comprises the several elements and the relation of one or more of such elements with respect to each of the others, and the apparatus embodying features of construction, combination(s) of elements and arrangement of parts which are adapted to effect such steps, all as exemplified in the following detailed disclosure, and the scope of the invention will be indicated in the claims.

BRIEF DESCRIPTION OF THE INVENTION

The device is explained in even greater detail in the following exemplary drawings. The drawings are merely exemplary to illustrate the structure of preferred devices and certain features that may be used singularly or in combination with other features. The invention should not be limited to the embodiments shown.

FIG. 1 is a front elevational view of an embodiment of a device;

FIG. 2A is a front elevational view of an embodiment of a drive assembly;

FIG. 2B is a front elevational view of an embodiment of a drive assembly;

FIG. 3 is a perspective view of an embodiment of an activator and a device;

FIG. 4A is a perspective view of an embodiment of an actuator;

FIG. 4B is an exploded perspective view of an embodiment of an actuator;

FIG. 5A is a schematic view of an embodiment of an activator and a magnet;

FIG. 5B is a schematic view of an embodiment of an activator and a magnet;

FIG. 5C is a schematic view of an embodiment of an activator and a magnet;

FIG. 5D is a schematic view of an embodiment of an activator and a magnet;

FIG. 6A is a schematic view of an embodiment of an actuator and a driving member;

FIG. 6B is a schematic view of an embodiment of an actuator and a driving member;

FIG. 6C is a schematic view of an embodiment of an actuator and a driving member;

FIG. 7 is a perspective view of an embodiment of an actuator and a driving member;

FIG. 9 is a perspective view of a section of an embodiment of a device;

FIG. 10 is a side elevational view of an embodiment of a clutch mechanism and an actuator;

FIG. 11 is a perspective view of an embodiment of a clutch mechanism;

FIG. 13 is a side elevational view of an embodiment of a clutch mechanism;

FIG. 14 is a side elevational view of an embodiment of an actuator;

FIG. 15 is a side elevational view of a clutch mechanism and an actuator;

FIG. 16 is a front elevational view of an embodiment of a device;

FIG. 17 is a perspective view of an embodiment of a device;

FIG. 18 is a perspective view of a portion of an embodiment of a device;

FIG. 19A is a top planar view of an embodiment of a device;

FIG. 19B is a cross-sectional view of the device of FIG. 19A taken along lines 19B-19B;

FIG. 19C is a top view of a section of the device of FIG. 19A;

FIG. 20 is a cross-sectional view of a section of the device of FIG. 19A taken along lines 20-20.

FIG. 21 is a front elevational view of an embodiment of a device;

FIG. 22 is a front elevational view of a section of the device of FIG. 21;

FIG. 23 is a top planar view of an embodiment of a device;

FIG. 24 is a top planar view of a section of the device of FIG. 24;

FIG. 25A is a front elevational view of an embodiment of a device;

FIG. 25B is a cross-sectional view of a section of the device of FIG. 25A taken along line 25B-25B;

FIG. 26 is a perspective view of an embodiment of a device;

FIG. 27 is a front elevational view of the device of FIG. 26;

FIG. 28 is a perspective view of a section of the device of FIG. 26.

DETAILED DESCRIPTION OF PREFERRED EMBODIMENTS

Certain exemplary embodiments of the invention will now be described with reference to the drawings. In general, such embodiments relate to a device for displacing tissue within the body of an animal, by way of non-limiting example, a person with spinothoracic deformity. A child with spinothoracic deformity often requires an implant periodically adjusted to expand the ribcage to permit organs to freely grow thereunder without being crowded. Accordingly, it is desirable to provide a device in accordance with an embodiment of the invention which provides remote adjustment of such an implant. Remote adjustment refers to the ability to adjust the device without having to undergo surgery or other invasive or non-invasive procedure.

Figure 8:
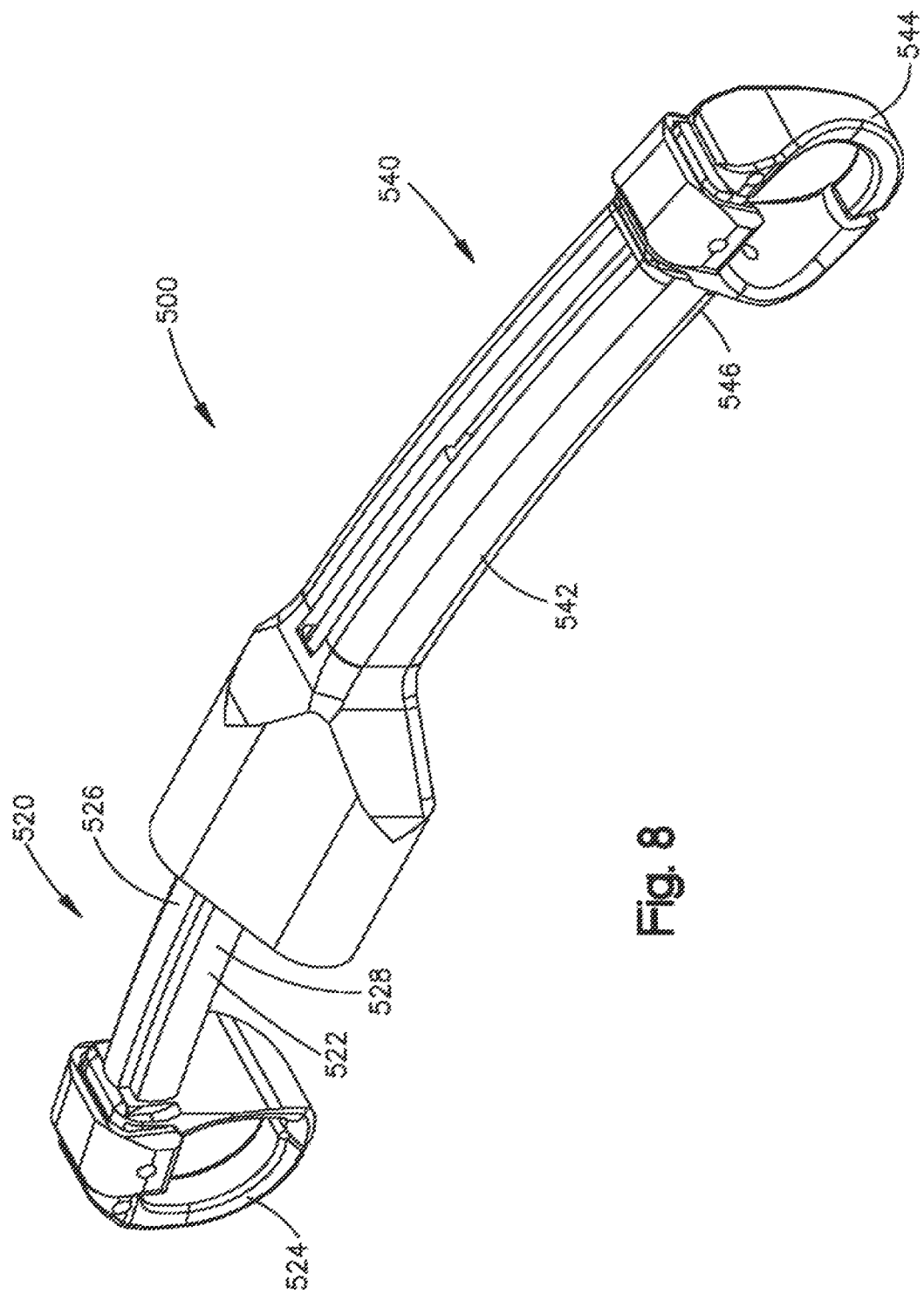
FIG. 8 is s perspective view of an embodiment of a device.

Reference is made generally to FIGS. 1-3 and 8-9, wherein certain exemplary embodiments of a device for displacing tissue are shown. Device for displacing tissue 100, 500 can be substantially straight, curved, or have another shape in accordance with design choice. In the embodiment shown, device 100,500 may include a first member 120, 520 having a rod 122, 522, which is preferably relatively smooth, and a second member 140, 540 having a tubular member 142, 542. Rod 122, 522 and tubular member 142, 542 are selectively displaceable with respect to each other, preferably telescopically or laterally displaceable. First member 120, 520 and second member 140, 540 are preferably elongated and may relatively straight or curved. Furthermore, it is to be understood that whereas certain embodiments are described herein as having a drive member associated with a tubular member, the drive member may be associated with a rod and vice versa In accordance with a preferred embodiment, device 100, 500 includes a drive assembly 200,600 which displaces first member 120, 520 from second member 140, 540 to extend and/or retract device 100, 500. Preferably, tubular member 142, 542 includes an inner cavity 146, 546 within which rod 122, 522 can be received.

In the embodiments shown, first member 120, 520 includes a first attaching device 124, 524 for attaching to a tissue within the body. Likewise, second member 140, 540 includes a second attaching device 144, 544 for attaching to a tissue within the body. The first and second attaching devices may be hooks, clamps, closed rings or other mechanisms that can attach to bone, for example, ribs. Examples of suitable clamps are described in U.S. Pat. No. 6,126,664 for "DEVICE AND METHOD FOR LOCATING AND RESECTING BONE;" U.S. Pat. No. 6,143,031 for "INTERVERTEBRAL IMPLANT WITH COMPRESSIBLE SHAPED HOLLOW ELEMENT;" U.S. Pat. No. 5,092,889 for "EXPANDABLE VERTICAL PROSTHETIC RIB;" U.S. Pat. No. 5,030,235 for "PROSTHETIC FIRST RIB;" and U.S. Pat. No. 5,261,908 for "EXPANDABLE VERTICAL PROSTHETIC RIB."

As device 100,500 is extended, first member 120, 520 may be displaced from second member 140, 540 and the respective tissues are pushed away from each other. For example, if first member 120, 520 is attached to a rib and second attaching device 140,540 is attached to the hip, the rib bone can be pushed outward to correct or treat a spinothoracic deformity.

Reference will be made to the embodiment shown in FIGS. 1-3, wherein a drive assembly 200 having a drive member 210 is shown. As shown, drive member 210 comprises an outer perimeter 214 preferably having at least a portion that is threaded 216, and preferably is attached to rod 122 of first member 120. As drive member 210 rotates, the threads 216 on the outer perimeter 214 may contact inner cavity 146, inner cavity 146 preferably having a threaded portion 148, and drive member 210 moves relative to the length of tubular member 142. Simultaneously, first member 120, which is attached to drive member 210, is also moved relative to the length of second member 140, preferably within second member 140, more preferably telescopically. Furthermore, the threads 216 of outer perimeter 214 of drive member 210 and the threaded portion 148 of inner cavity 146 of second member 210 cooperate to prevent slippage and retain first member 120 and second member 140 in position. Whereas drive member 210 is shown as being attached to an end of rod 122, it is to be understood that drive member 210 can be attached to rod 122 at another location relative to the length of rod 122. It is to be understood that the term "rotation" encompasses a partial rotation less than 360°, a complete rotation of 360° or greater.

Drive member 210 can be rotated by an actuator 300 for example as shown in FIGS. 4A,B. Actuator 300 preferably includes a magnetic member, preferably a magnet 310, and which is preferably activated by an external magnetic activator 400. The embodiment of the actuator 300 illustrated is aligned with, preferably concentric with, drive member 210, and includes a magnet 310, preferably a cylindrical magnet having a first pole 312 and a second pole 314, and a ring 320 preferably attached to magnet 310 such that the rotation of magnet 310 causes ring 320 to rotate. An alternate embodiment of the actuator may be arranged parallel to, preferably offset from the drive member.

By way of non-limiting example, first pole 312 can be a north pole and second pole 314 can be a south pole. As magnet 310 rotates, drive member 210 is rotated, preferably in predetermined increments, thus extending or refracting device 100 in predetermined increments. Magnet 310 can be rotated by a magnetic field external to the body, thus eliminating the need for an incision or invasive procedure to extend or retract device 100. By providing a remotely adjustable device, the patient can be saved from the surgical procedures otherwise necessary, and the risk of infection and hospitalization associated therewith. Additionally, the aligned, preferably concentric, arrangement of actuator 300 and drive member 210 can provide a substantially narrow device having a low profile, which may reduce patient discomfort and cause less tissue irritation.

An embodiment of external activator 400 is illustrated in FIGS. 3, 5A-D and preferably includes a face 440 having two or more, preferably four magnets 420a, 420b having a single pole each mounted on face 440. As shown in FIG. 3, external activator 400 is preferably located above skin S. In the embodiment shown, external activator 400 includes two magnets 420a having a north pole and two magnets 420b having a south pole. The north poled magnets 420a and the south poled magnets 420b are arranged in an alternating order. As face 440 is rotated about an axis X by an activator bar 460, a magnetic field can be created. Referring to FIGS. 5A-D, the arrangement of single pole magnets 420a,b can provide the desired rotation of magnet 310 as external activator 400 is rotated. As the single pole magnets 420a,b move toward or away from actuator 300, magnets 420a,b create an attraction (solid arrows) and/or a rejection force (dashed lines) with magnet 310 to rotate magnet 310.

Preferably, magnet 310 is attached to a ring 320 having a ring rod 326 extending through the center of magnet 310 and a ring tab 322 as illustrated in FIG. 4B. Ring 320 preferably comprises a durable material, such as a hard metal, more preferably a material that is not magnetic and thus unaffected by the external activator 400. Likewise, it is preferably for drive member 210 not to be magnetic. Ring 320 and magnet 310 can be attached, preferably permanently attached, for example, using an adhesive, a groove and projection, etc. Ring 320 can also include a projection 324 extending away from magnet 310 about which drive member 210 can rotate.

Referring to the embodiment of actuator 300 shown in FIGS. 5-7, when magnet 310 is rotated by external activator 400, ring 320 also rotates and ring tab 322 contacts and pushes a tooth 212 of drive member 210 to rotate drive member 210. The actuator 300 may provide continuous rotation of drive member 210 with the continued rotation of magnet 310 to provide a smooth, continuous displacement of rod 120. Alternatively, drive member 210 may be rotated in increments of varying force or oscillate to obtain the necessary torque to rotate drive member 210 as described in more detail below.

In accordance with one embodiment of the device, actuator 300 can extend device 100 by rotating drive member 210 in one direction and retract device 100 when rotating in the opposite direction. Alternatively, actuator 300 can rotate drive member 210 in one direction to extend device 100 without permitting retraction. Other options for the relationship between actuator and drive assembly 200 are also available.

Drive member 210 preferably can be rotated if the static torque, namely the rotational force of actuator 300 as magnet 310 rotates, is greater than the work torque, namely the rotational force required to rotate drive member 210. Various factors may affect the work torque, such as the load on the implant, the thread pitch, the friction, etc. The static torque can be dependent on various factors, such as, by way of non-limiting example, the distance between actuator 300 and external activator 400, and the magnet material properties. Therefore, the static torque may be predetermined during manufacture. Once the work torque becomes greater than the static torque, actuator 300 does not rotate drive member 210 and magnet 310 ceases to rotate, preferably with ring tab 322 proximate tooth 212. Magnet 310 can then rotate in the opposite direction such that ring tab 322 rotates away from tooth 212, preferably about 180°. Preferably, magnet 310 ceasing to rotate and subsequently rotating in the opposite direction occurs relatively quickly, more preferably such that magnet 310 appears to bounce back upon ring tab 322 contacting tooth 212. Meanwhile, activator 400 preferably continues to rotate in a consistent direction without oscillating. The degree of rotation of magnet 310 away from tooth 212 may be determined, for example, by the number of poles on the magnet 310 or actuator 300. Therefore, ring tab 322 can be accelerated over a rotary angle of 180°, thus creating a greater static torque. Various factors may affect the static torque, such as the magnetic material, the mass, the diameter, the activator velocity, and the like. Such an effect may be referred to as a "sledge hammer" effect due to the repeated impacting of the rotating ring tab 322. Such a relationship is illustrated in FIGS. 6A-C, wherein ring tab 322 retracts further and further away from tooth 322 to create a greater rotary angle and thus a greater static torque. Therefore the torque applied on drive member 210 may be substantially greater than the direct torque applied by the rotating magnet. Preferably, such a static torque is about 2 to 15 times greater, more preferably about ten times greater than the static torque of a rotating magnet 310.

In the embodiment shown in FIG. 2A, actuator 300 includes a magnet 310 that may be attached to a ring 320 at one end, and an end piece 330 at the opposite end that preferably prevents magnet 310 from being moved away from ring 320. Furthermore, actuator 300 may include an axis, such as an axle 340 about which magnet 310 and ring 320 can rotate, which preferably provides a gap and a relatively low friction coefficient between ring 320 and drive member 210 and between magnet 310 and end piece 330.

Figure 12A:
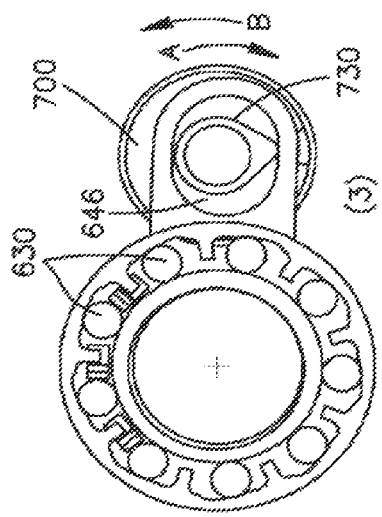
FIG. 12A is a side elevational view of the clutch mechanism and the actuator of FIG. 10 in a first position.
Figure 12D:
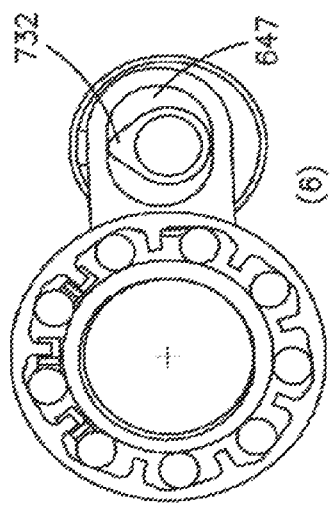
FIG. 12D is a side elevational view of the clutch mechanism and the actuator of FIG. 10 in a fourth position.
Figure 12B:
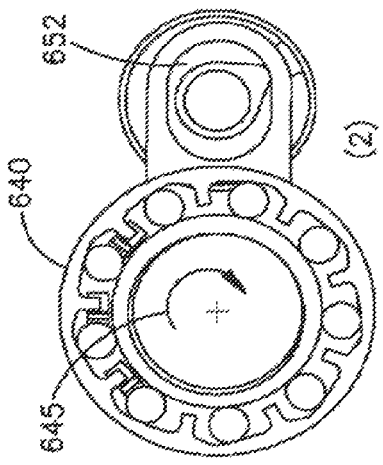
FIG. 12B is a side elevational view of the clutch mechanism and the actuator of FIG. 10 in a second position.
Figure 12E:
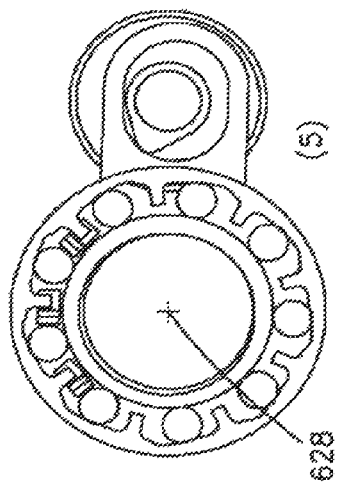
FIG. 12E is a side elevational view of the clutch mechanism and the actuator of FIG. 10 in a fifth position.
Figure 12C:
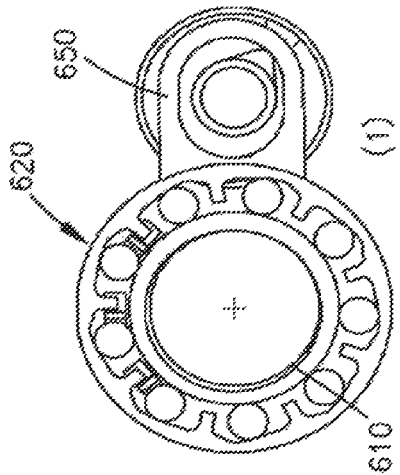
FIG. 12C is a side elevational view of the clutch mechanism and the actuator of FIG. 10 in a third position.
Figure 12F:
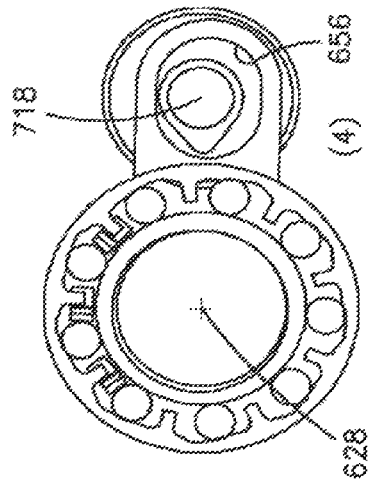
FIG. 12F is a side elevational view of the clutch mechanism and the actuator of FIG. 10 in a sixth position.
Figure 12I:
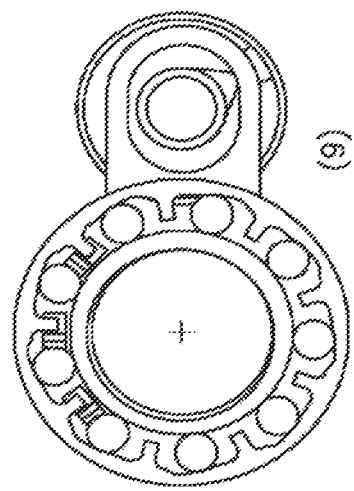
FIG. 12I is a side elevational view of the clutch mechanism and the actuator of FIG. 10 in a ninth position.
Figure 12H:
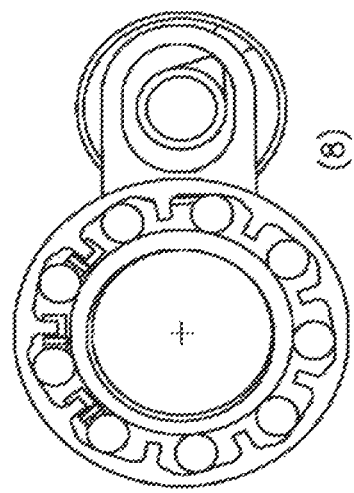
FIG. 12H is a side elevational view of the clutch mechanism and the actuator of FIG. 10 in a eighth position.
Figure 12G:
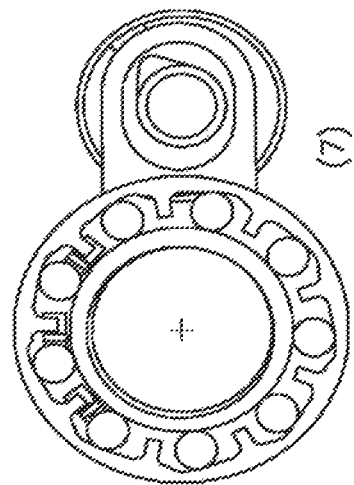
FIG. 12G is a side elevational view of the clutch mechanism and the actuator of FIG. 10 in a seventh position.

Reference will now be made to FIGS. 8-15, wherein certain embodiments of the device include first member 520 displaceable relative to the length of second member 540 by a drive assembly 600, and further includes an actuator 700 that is adjacent to drive assembly 600. In the embodiments shown, first member 520 includes a rod 522 having an outer perimeter 526 that is at least partially threaded 528 and second member 540 includes a tubular member 542 having an inner cavity 546 that is preferably substantially smooth. Drive assembly 600 includes a drive member 610 preferably having a generally cylindrical shape and an outer perimeter 614. Drive member 610 comprises an inner surface 616, at least a part of which is threaded and contacts the outer perimeter 526 of rod 522 of first member 520, which is also at least partially threaded, thus permitting drive member 610 to move relative to the length of rod 522. Preferably, drive member 610 is concentrically aligned with rod 522.

Whereas a variety of drive assemblies can be used in accordance with the device, one embodiment of a suitable drive assembly 600 is shown in FIGS. 9-13. In the embodiment shown, drive assembly 600 includes a clutch mechanism, for example, a freewheel clutch 620 as shown in FIGS. 10-13 having one or more, preferably a plurality of stoppers such as needles or rollers 630 surrounded by an outer housing 620 which is preferably aligned with, more preferably concentrically aligned with, drive member 610. As shown, freewheel clutch 620 includes outer housing 640 surrounding and preferably concentrically aligned with drive member 610. Freewheel clutch 620 has a plurality of needles or rollers 630 positioned between outer housing 640 and drive member 610. In the embodiment of freewheel clutch 620 shown, outer housing 640 has inner walls 626 having an incline such that inner walls 626 include converging walls 626a.

Therefore, when outer housing 640 is rotated in one direction, for example, in a clockwise direction, needles 630 can move, preferably roll, until they are wedged between converging walls 626a and outer perimeter 614 of drive member 610 which stops further movement of the rollers 630. When the rollers 630 are wedged and stop moving, a rotational force is transferred to the drive member 610, thus rotating drive member 610. Freewheel clutch 640 can also include one or more springs 622 which urge needles 630 toward converging walls 626a.

On the other hand, if outer housing 640 is rotated in the opposite direction, namely, in a counter-clockwise direction, needles 630 can be released to move, preferably roll, toward diverging walls 626b of outer housing 640. The work torque required to rotate drive member 610 in a counter-clockwise direction is preferably greater than the force necessary for needles 630 to move or roll around the outer perimeter 614 of drive member 610. Therefore needles 630 can roll toward diverging walls 626b while drive member 610 remains in place. Accordingly, freewheel clutch 640 may provide a ratcheting effect by providing a clockwise rotation but not a counter-clockwise rotation of drive member 610. Whereas FIGS. 10-12 show nine needles 630, it is to be understood that the number of needles 630 can be varied as a matter of design choice and to fit the desired application. By way of non-limiting example, as shown in FIG. 13, an alternate embodiment of freewheel clutch 620 includes six needles 630. Additionally, whereas rollers 630 of freewheel clutch 620 are positioned equidistant from each other, the rollers need not be equidistant as illustrated in the embodiment of FIG. 13. Moreover, in accordance with the embodiment of the freewheel clutch shown, outer housing 640 may have a partially flattened portion 642 which may provide a relatively low profile of device and reduce discomfort and cause less tissue irritation.

An embodiment of drive assembly 600 as shown in FIGS. 10-12 includes a lever 650 extending radially outward from freewheel clutch 620 and peripherally fixed thereto, lever 650 having an aperture generally indicated at 652 having an aperture surface 656. Lever 650 is preferably displaced by an actuator 700 comprising a rotating member 730 preferably having a generally cylindrical shape and a bulbous projection 732 that extends radially outward. By way of non-limiting example, rotating member 730 can be an eccentric cam or disc. In accordance with a preferred embodiment of drive assembly 600 and actuator 700, bulbous projection 732 contacts aperture surface 656 as at least a portion of rotating member 730 rotates within aperture 656. As bulbous projection 732 contacts and moves along aperture surface 656, lever 650 can be selectively displaced.

Preferably, as shown in FIG. 9, actuator 700 can include a magnet 710, preferably a cylindrical magnet, which can be rotated by an external magnetic field. In the embodiment shown, actuator 700 includes a non-magnetic, hard metal ring 720 having a ring tab 722. For example, actuator 700 can be similar to actuator 300 of FIG. 3 described above, wherein a ring tab 722 can contact a rotating member 730 to force rotation of rotating member 730 about an actuator rod 750. In accordance with one embodiment of actuator 700, ring tab 722 can push bulbous projection 732 as ring tab 722 rotates. Alternatively, rotating member 730 can include a tooth 734 extending toward ring 720, which ring tab 722 can contact, resulting in rotating member 730 rotating. Such a relationship is described in detail above. Both embodiments can provide the "sledge hammer" effect. Alternatively, rotating member 730 can be rotated by magnet 710 directly, thus maintaining the same torque as the rotating magnet 710. Additionally, actuator 700 can include a reduction gear, for example, a gear train such that a plurality of rotations of magnet 710 can result in a single rotation of a gear at a greater torque. It is to be understood that other embodiments of the actuator are within the scope of the invention as a matter of design choice.

An example of the way in which freewheel clutch 620 works is illustrated in FIGS. 12A-I, wherein the sequential relationship between drive assembly 600 and rotating member 730 is illustrated in positions (1)-(9) as rotating member 730 is rotated in a clockwise direction. In position (1), bulbous projection 732 contacts the aperture surface 656 of lever 650. As rotating member 730 rotates, bulbous projection 732 moves along aperture surface 656 in a clockwise direction and pushes lever 650 in direction A, thus rotating outer housing 640 in a clockwise direction as shown in subsequent positions (2) and (3). In the embodiment shown, the clockwise rotation of outer housing 640 results in the rotation of drive member 610 in the clockwise direction as indicated by the arrows 645.

Preferably, as outer housing 640 rotates in a clockwise direction, needles 630 are stopped by converging inner walls 626a of outer housing 640 until needles 630 are wedged between converging walls 626a and outer perimeter 614 of drive member 610. A clockwise torque is preferably generated, for example, by a frictional force evoked by the wedged needles 630. Therefore, the greater the torque generated, the more needles 630 may become wedged, thus increasing the frictional force between outer perimeter 614 of drive member 610 and needles 630 and substantially preventing needles 630 from sliding or rolling along outer perimeter 614 of drive member 610. Therefore, as outer housing 640 continues to rotate, drive member 610 can be rotated in a clockwise direction. Position (3) shows drive assembly 600 when lever 650 is displaced the maximum distance in direction A. Once this position (3) is passed, bulbous projection 732 enters a clearance 646 in aperture 652 in position (4) such that as rotating bulbous projection 732 continues to rotate in a clockwise direction, lever 650 is not displaced.

As rotating member 730 continues to rotate in the clockwise direction, bulbous projection 732 moves along aperture surface 656 of lever 650 as shown in position (5) and displaces lever 650 in direction B until lever 650 is displaced the maximum distance in direction B as shown in position (6). As lever 650 is displaced in direction B, outer housing 640 rotates in a counter-clockwise direction. By way of non-limiting example, as outer housing 640 rotates in a counter-clockwise direction, needles 630 are permitted to roll toward diverging walls 626b of outer housing 640. Therefore, outer housing 640 can rotate in a counter-clockwise direction without resulting in the rotation of drive member 610, thus preferably providing a ratcheting effect.

Once the maximum displacement of lever 650 in direction B is reached, bulbous projection 732 preferably enters a clearance 647 in aperture 652 such that as rotating bulbous projection 732 continues to rotate in a clockwise direction, lever 650 is not displaced, as shown in positions (7)-(8). In the embodiment shown in FIG. 12, once position (9) is reached, bulbous projection 732 has rotated 360° and has returned to position (1), and the process can be repeated until the desired rotation of drive member 610 is reached, and thus the desired extension or retraction of device 500. It is to be understood that the magnet may also rotate in the other direction.

Accordingly, drive assembly 600 preferably provides a ratcheting effect, by rotating drive member 610 in one direction and not the other, while lever 650 is displaced back and forth in directions A and B.

Referring to FIG. 14, the coordination of drive assembly 600 and actuator 700 can provide a magnified torque on drive member 610 compared to the torque of the rotating magnet 710 or rotating element 730. The smaller the angle a, the smaller the distance L and greater the force F 1. Therefore, the smaller the initial angle, the less movement of lever 650 is generated. Accordingly, bulbous projection 732 preferably contacts lever 650 at approximately 45°, and the preferred displacement D of lever 650 in direction A is approximately 0.2 mm. This can provide a total displacement of lever 650 of about 0.4 mm and a rotation of 2.3° with lever 650 having a length of about 10 mm between a center 718 of magnet 710 and a center 628 of freewheel clutch 620. It to be understood that the identified dimensions and angles are merely exemplary and not intended to limit the scope of the invention. Rather, the dimensions and angles can be varied as a matter of application specific design choice without deviating from the scope of the invention.

In accordance with another embodiment of the drive assembly 660 as shown in FIG. 15, drive assembly 660 can include a drive member 662 having a plurality of teeth 664 and grooves 668 within an outer housing 661, drive member 662 being preferably concentrically aligned with outer housing 661. Outer housing 661 is preferably associated with a lever 670 having a shaft 672 having a projection 674 constructed and arranged to be selectively received within grooves 668 of drive member 662.

As illustrated in FIG. 15, as lever 670 is displaced in direction A, projection 674 of shaft 672 is received within a groove 668 of drive member 662 and applies a force in direction A, thus rotating drive member 662 in a clockwise direction. When lever 670 is displaced in direction B, however, because of the angle of teeth 664 and projection 674 of shaft 672, projection 674 of shaft 672 glides across teeth and thus drive member 660 does not rotate in the clock-wise direction, thus creating a ratcheting effect. The displacement of lever 670 can be activated by a magnetic actuator, for example, actuator 700 as illustrated in FIG. 9.

Whereas an embodiment of drive assembly 600 having a lever 650 has been illustrated herein as rotating drive member 610 along rod 522 of first member 520, it is to be understood that drive member 610 can be rotated within tubular member 542 of second member 540 without deviating from the scope of the invention. Likewise, whereas an embodiment of drive assembly 200 having a magnetic actuator 300 coaxial thereto is illustrated as rotating drive member 210 within the threaded inner cavity 146 of tubular member 142, it is to be understood that drive member 210 can be rotated along rod 122 of first member 120 as a matter of design choice without deviating from the scope of the invention. Alternate embodiments are also contemplated.

Additionally, it may be preferable for drive assembly 600 and actuator 700 to be enclosed in a housing to at least substantially prevent tissue irritation during the rotation of the magnet 719 or drive member 610.

Referring to FIGS. 16-20, an embodiment of a device 900 can include a first member 920 and a second member 940 that are selectively displaceable relative to each other, preferably along the length of one another, more preferably telescopically displaceable, by a drive assembly 950 having a drive member 942. First member 920 can include an elongated rod 922 and second member 940 can include an elongated tubular member 942 within which elongated rod 922 can be telescopically displaced to extend or retract device 900. Alternatively, first member 920 and second member 940 can be constructed and arranged such that as device 900 extends and contracts, a part of first member 920 moves along the side of a part of second member 940, such as for example adjacent rods. Drive member 952 as shown may be fixed, preferably permanently, to tubular member 942, wherein drive member 952, and thus tubular member 942, can move relative to the length of rod 922.

Preferably, certain embodiments of the device, for example, device 900 in FIG. 16, has a curvature, and more preferably has a radius of curvature of about 220 mm. Such curvature may be beneficial for use with a spine, for example, within a chest wall. Additionally, device 900 may be constructed to substantially minimize tissue resistance, for example, when device 900 is being extended. Referring to FIG. 18, tubular member 942 may include a relatively sharp edge 944 which preferably cuts through the tissue within a patient's body as device 900 is being extended. Such a sharp edge 944 may be additionally helpful, for example, when a portion 946 of tubular member 942 projects away from rod 922. Whereas portion 946 can be utilized for a variety of functions, portion 946 may be utilized to manually push tubular member 942, or portion 946 can house a lever, actuator, magnet, gears, and the like.

In accordance with a preferred embodiment of rod 922 as shown in FIGS. 19A-C, rod 922 includes a generally cross-shaped or (X shape) cross section, four sides 924a,b, 926a,b and has at least a partially threaded portion 928. As shown, rod 922 can include two threaded sides 924a,b having a first radius of curvature, and two smooth sides 926a,b having a second radius of curvature preferably different from the first curvature, wherein threaded sides 924a,b and smooth sides 926a,b are alternatingly positioned around the perimeter of rod 922.

Preferably, drive member 952 includes a threaded portion 954 which can contact threaded sides 924 to move relative to the length of rod 922 as well as remain in place without slipping. Smooth sides 926a,b preferably do not contact drive member 952 and therefore do not create interference against drive member 952. More preferably, smooth sides 926a,b have a smaller diameter than threaded sides 924a,b, thus facilitating not contacting drive member 952.

Additionally, referring to the embodiment shown in FIGS. 16 and 19B, device 900 may have a top 912a and a bottom 912b, wherein device 900 curves from top 912a toward bottom 912b. Threaded sides 914a,b may be proximate the sides 916 of device 900. Preferably, referring to FIG. 19B, threaded sides 924a,b are not proximate bottom 912b where the distance between the threads may decrease, thus creating clumping of threads. Furthermore, providing a smaller diameter of smooth sides 926a,b may prevent jamming the bottom of drive member 952. It is to be understood that rod 922 may include more or less threaded sides 924a,b or smooth sides 926a,b, and the positioning of threaded sides 924a,b and smooth sides 926a,b on rod 922 may be altered as a matter of design choice.

Referring to FIGS. 19A and 19C, tubular member 942 may include a slot generally indicated at 944 through which rod 922 can be seen and accessed. This embodiment of device 900 can facilitate manufacture by providing slot 944 for access by a machine tool while maintaining device 900 relatively compact.

FIG. 20 illustrates a cross section of an exemplary embodiment of drive member 952 positioned along the length of rod 922, the cross section take along line 20-20 of FIG. 19A. Drive member 952 preferably comprises a generally cylindrical shape and a threaded portion 954 proximate the middle region of drive member 952, threaded portion 954 constructed and arranged to contact threaded sides 924 of rod 922 preferably with non-threaded regions proximate both end portions 956. Drive member may be operably associated with a rotating mechanism, such as a freewheel clutch 958 for rotating drive member 952. Preferably, threaded portion 954 is approximately 4 mm long, and end portions 956 of drive member 952 do not include threads. There is preferably no interference between end portions 956 and rod 922, which may facilitate the rotation of drive member 952 along rod 922 having a curvature.

Referring to FIGS. 21-22, a device 1000 can include two or more first members 1020 having rods 1022, two or more second members 1040 having tubular members 1042, two or more drive members 1110 associated with, preferably fixed to rods 1022 and located within tubular members 1042, and an actuator 1100 having a magnet 1120. Rods 1022 and tubular members 1042 may be relatively curved or straight, more preferably straight. In accordance with a preferred embodiment, device 1000 may include two relatively straight first members 1020 positioned at an angle with respect to each other. Therefore, device 1000 may better fit the body of the patient while facilitating manufacture.

In the embodiment shown, magnet 1120 is a rotatable magnet associated with rods 1022 such that the rotation of magnet 1120 results in the rotation of rods 1022, preferably simultaneously. Actuator 1100 is preferably associated with rods 1022 via a flexible coupling 1002, such as a cardan coupling or universal joint. Drive member 1110 can be associated with, preferably fixed to, rods 1022, such that the rotation of rods 1022 rotates drive members 1110. Magnet 1120 preferably can be rotated by an actuator located outside the skin.

In accordance with an embodiment of device 1000, as magnet 1120 rotates, rods 1022 are rotated, thus rotating drive members 1110 located within tubular member 1042. Tubular member 1042 preferably includes an inner cavity 1046 having a threaded region 1044. Drive members 1110 preferably include a threaded region 1114 on its outer perimeter 1112, thus contacting threads 1044 of tubular members 1042 to move drive members 1110 relative to the length of tubular members 1042.

Second members 1040 can include an attaching element 1044 to attach to tissue in the body of an animal and a tubular member 1042. Therefore, as first members 1020 are displaced relative to the length of second members 1040, device 1000 can be extended or retracted accordingly, thus moving the tissues of the body closer together or further apart. Such an arrangement may facilitate manufacturing device 1000, and can be beneficial by partially straightening out as device 1000 is extended, especially in patients where a device having a fixed curvature may lead to a too strong kyphosis when fully expanded. Furthermore, drive assembly 1100 preferably remains fixed within the patient's body regardless of how much device 1000 is extended or retracted.

In accordance with the embodiment shown in FIG. 22, first members 1020 include housings 1024 for enclosing rods 1022. Housings 1024 may include grooves 1026, preferably running externally along the length of housing 1024. Tubular members 1042 may include projections or pins 1046 projecting toward housings 1024. Pins 1046 are preferably constructed and arranged to be received within groove 1026 to substantially prevent the rotation of tubular member 1042 with respect to housing 1024 and vice versa, thus substantially preventing device 1000 from rotating within the patient's body.

FIGS. 23-24 illustrate an embodiment of device 1200 having a first freewheel clutch 1210 for two or more rotating rods 1222 in a first direction, and a second freewheel clutch 1220 to prevent rods 1222 from rotating in a second direction opposite to the first direction. Preferably, first freewheel clutch 1210 is associated to a magnet 1230, and second freewheel clutch 1220 is associated with, preferably fixed to, a housing 1240 substantially enclosing second freewheel clutch 1220. A device 1200 as described may be beneficial in situations when each rotation of first freewheel clutch 1210 is insufficient to transfer enough torque to rotate drive members 1260. In such a situation, rods 1222 may oscillate back and forth without rotating drive members 1260. Second freewheel clutch 1220 may at least substantially prevent the oscillation of rods 1222 by preventing the reverse rotation of rods 1222.

FIGS. 25A-B illustrate another embodiment of device 1050 having two attaching members 1070, each attaching member 1070 having a rod 1074. Device 1050 may further include one or more connecting members 1060 to connect the two attaching members 1070 to each other. Attaching members 1070 may have an attachment mechanism 1052 for attaching to the tissue, such as a bone, in a body. Referring to FIGS. 25A-B, connecting member 1060 may include two tubular members 1062 arranged at an angle less than 180 degrees relative to each other, tubular member 1062 constructed and arranged to receive rod 1074. Tubular member 1062 may be connected to a driving member 1066, driving member 1066 preferably rotatable about rod 1074, wherein rod 1074 may include a threaded region 1076. Driving member 1066 may include a threaded inner perimeter 1068 constructed and arranged to contact threaded region 1076 of rod 1074 to displace attaching member 1070 relative to connecting member 1060.

Referring to the embodiment of FIGS. 25A-B, connecting member 1060 may include an actuator, for example, a rotatable magnet 1064 connected to a contact member 1065. Preferably, contact member 1065 includes a tab 1065*a* for contacting a tooth 1066*a* of driving member 1066. When tab 1065*a* contacts tooth 1066*a* with sufficient torque, driving member 1066 may rotate, thus displacing attaching member 1070 relative to connecting member 1060. Preferably, magnet 1064 can oscillate to provide a ratcheting effect on driving member 1066. In the embodiment shown, device 1050 includes two magnets 1064 which are arranged such that a common activator may be utilized to rotate both magnets 1064 in the same direction, thus displacing both attaching members 1070 relative to connecting member 1060.

Attaching member 1070 preferably includes a housing 1072 constructed and arranged to contain rod 1074 and also possibly a portion, if any, of tubular member 1062. Whereas attaching member 1070 is described herein as including rod 1074 and connecting member 1060 is described herein as including tubular member 1062, it is contemplated that attaching member 1070 may include tubular member 1062 and connecting member 1060 may include rod 1074.

Reference is now made to FIGS. 26-27, wherein an embodiment of device 1300 is illustrated having a first member 1310 having a rod 1312 and a second member 1320 having a tubular member 1322, further including a drive assembly 1330 associated with rod 1312 for selectively displacing first member 1310 with respect to second member 1320. More specifically, drive assembly 1330 may include a magnetic actuator 1332 for activating a first freewheel clutch 1334 which preferably rotates a shaft 1336 which winds a cable 1340 preferably about shaft 1336. In the embodiment shown, cable 1340 is received within a channel 1313*a* which runs along the length of rod 1312 on a first side 1314 and a channel 1313*b* which runs along the length of rod 1312 on a second side 1315 such that when cable 1340 is being wound about shaft 1336, cable 1340 moves in a first direction C in channel 1313*a* and in a second direction D, preferably different from first direction C, in channel 1313*b*. Whereas FIGS. 26-28 illustrated an embodiment of device 1300 wherein first side 1314 is different from second side 1315, it is to be understood that first side 1314 and second side 1315 may be the same side as a matter of design choice. Preferably, a first end 1342 of cable 1340 is connected, more preferably fixed, to tubular member 1322. Therefore, as first freewheel clutch 1334 is rotated, cable 1340 is wound about shaft 1336 and first end 1342 of cable 1340 is pulled in direction D, thus displacing tubular member 1322 in direction D, away from drive assembly 1330 and thus extending device 1300. Drive assembly 1330 may also include a second freewheel clutch 1339 connected to shaft 1336 to prevent the reverse rotation of shaft 1336.

One embodiment of the actuator may include a gear train. For example, in an actuator having a magnet that rotates a rotating member which in turn rotates the drive member, a gear train can be provided between the magnet and the rotating member, or between the rotating member and the drive member as a matter of design choice. It is to be understood that a gear train may be provided at various portions of the device, such as the drive assembly.

One preferred embodiment of the device has a length of about 10 to 200 mm, more preferably about 20 to 180, most preferably about 30 to 150 mm when fully contracted. Additionally, one embodiment of the device has a length of about 20 to 400 mm, more preferably about 30 to 350 mm, most preferably about 40 to 300 mm when fully extended. The radius of curvature of the device is preferably between about 100 and 300 mm, more preferably between about 150 and 250 mm, most preferably about 220 mm. However, it is to be understood that the preferred shape, length, curvature, and the like, of the device varies according to the body in which the device is to be inserted, preferably implanted.

Additionally, whereas certain embodiments of the driving member are described herein as having external threading, one of ordinary skill in the art would appreciate that the embodiments of the drive member may have internal threading, and vice versa, as a matter of design choice. For example, providing internal threading may provide an increased driving force.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

We claim:

1. A bone displacement apparatus comprising: a first bone attachment member; a second bone attachment member; and a displacement mechanism configured for subcutaneous implantation in a position accessible by a magnetic field transmitted through skin, the displacement mechanism comprising a rod operatively coupled to the first bone attachment member, a drive member operatively attached to the rod, the drive member having first screw threads, a tubular member operatively coupled to the second bone attachment member, an inner surface of the tubular member having second screw threads to engage the first screw threads, and a magnet rotatable back and forth in opposite directions, wherein when an external rotating magnetic force is applied to a magnet, the rod moves in a displacement direction in accordance with a rotational interaction of the first screw threads and second screw threads, wherein the drive member is driving by a ring having a tab that contacts a tooth of the drive member.

2. The apparatus of claim 1, wherein the rod is directly connected to the first bone attachment member.

3. The apparatus of claim 1, further comprising an actuator operative to generate and transmit a rotating magnetic field to the magnet through the skin.

4. The apparatus of claim 3, wherein the actuator is aligned with the drive member.

5. The apparatus of claim 1, wherein the displacement mechanism moves the first bone attachment member axially relative to the second bone attachment member upon rotation of the rod in a displacement direction.

6. The apparatus of claim 5, wherein the displacement mechanism is rotatable in a first direction to displace the first attachment member away from the second attachment member, and the displacement mechanism is rotatable in a second direction to displace the first attachment member toward from the second attachment member.

7. The apparatus of claim 1, wherein the second screw threads extend substantially along a length of the tubular member to engage the first screw threads.

8. The apparatus of claim 1, wherein the first bone attachment member and the second bone attachment member are curved.

\* \* \* \* \*